(12) United States Patent
Aoki et al.

(10) Patent No.: US 9,890,110 B2
(45) Date of Patent: Feb. 13, 2018

(54) METHOD FOR PRODUCING AMIDE DERIVATIVE

(71) Applicant: Mitsui Chemicals Agro, Inc., Minato-ku, Tokyo (JP)

(72) Inventors: Youji Aoki, Chiba (JP); Yumi Kobayashi, Mobara (JP); Hidenori Daido, Otsu (JP); Hiroyuki Katsuta, Chiba (JP); Hidetaka Tsukada, Omuta (JP); Atsushi Hirabayashi, Omuta (JP); Yusuke Takahashi, Omuta (JP); Michikazu Nomura, Mobara (JP); Atsuko Kawahara, Mobara (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

(21) Appl. No.: 15/185,586

(22) Filed: Jun. 17, 2016

(65) Prior Publication Data

US 2016/0297750 A1    Oct. 13, 2016

Related U.S. Application Data

(62) Division of application No. 14/306,885, filed on Jun. 17, 2014, now Pat. No. 9,394,240, which is a division of application No. 13/058,349, filed as application No. PCT/JP2009/064295 on Aug. 13, 2009, now Pat. No. 8,853,440.

(30) Foreign Application Priority Data

Aug. 13, 2008    (JP) .................................. 2008-208714

(51) Int. Cl.
*C07C 233/76*    (2006.01)
*A01N 37/46*    (2006.01)
(Continued)

(52) U.S. Cl.
CPC ............ *C07C 233/76* (2013.01); *A01N 37/46* (2013.01); *A01N 43/40* (2013.01); *C07C 205/58* (2013.01);
(Continued)

(58) Field of Classification Search
USPC .................................................. 558/415, 416
See application file for complete search history.

(56) References Cited

U.S. PATENT DOCUMENTS

2009/0099204 A1* 4/2009 Yoshida ................ A01N 37/46
514/255.06
2009/0162453 A1    6/2009 Kawahara et al.
(Continued)

FOREIGN PATENT DOCUMENTS

CN    101203485    6/2008
CN    101208009    6/2008
(Continued)

OTHER PUBLICATIONS

International Search Report dated Sep. 29, 2009.
(Continued)

*Primary Examiner* — Pancham Bakshi
(74) *Attorney, Agent, or Firm* — Rankin, Hill & Clark LLP

(57) ABSTRACT

An amide derivative represented by Formula (3), which exhibits excellent efficacy in pest control effect, is produced by allowing a compound represented by the following Formula (1) and a compound represented by Formula (2) to react with each other. In Formula (1) to Formula (3), $Y^1$ and $Y^2$ each represent a halogen atom or a haloalkyl group; Rf represents a $C_3$-$C_4$ perfluoroalkyl group; and $R^1$ and $R^2$ each represent a hydrogen atom or an alkyl group; LG represents a leaving group; T represents a hydrogen atom or a fluorine atom; $X^1$, $X^3$, $X^4$, and $X^5$ each represent a hydrogen atom, a halogen atom, or the like; and A represents a nitrogen atom, a methine group, or the like.

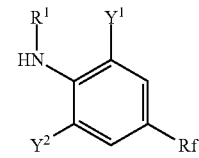

(1)

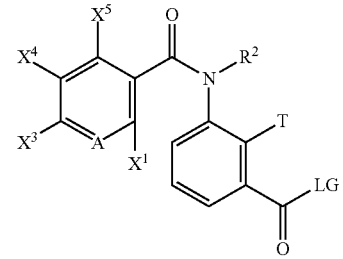

(2)

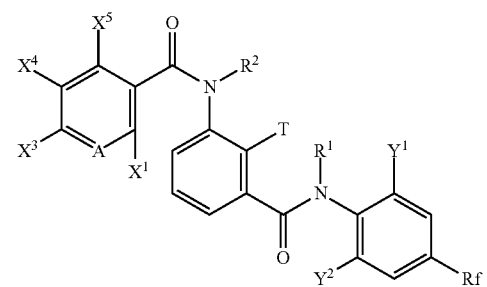

(3)

1 Claim, No Drawings

(51) Int. Cl.
*A01N 43/40* (2006.01)
*C07C 205/58* (2006.01)
*C07C 231/02* (2006.01)
*C07C 233/81* (2006.01)
*C07C 255/57* (2006.01)
*C07D 213/82* (2006.01)
*C07C 235/68* (2006.01)
*C07C 255/58* (2006.01)

(52) U.S. Cl.
CPC .......... *C07C 231/02* (2013.01); *C07C 233/81* (2013.01); *C07C 235/68* (2013.01); *C07C 255/57* (2013.01); *C07C 255/58* (2013.01); *C07D 213/82* (2013.01)

(56) References Cited

U.S. PATENT DOCUMENTS

| | | |
|---|---|---|
| 2009/0192167 A1 | 7/2009 | Nomura et al. |
| 2013/0317247 A1 | 11/2013 | Kitajima et al. |

FOREIGN PATENT DOCUMENTS

| | | |
|---|---|---|
| EP | 1911751 | 4/2008 |
| EP | 1912933 | 4/2008 |
| EP | 1913815 | 4/2008 |
| EP | 1916236 | 4/2008 |
| EP | 1938685 | 7/2008 |
| JP | 2007-031324 | 2/2007 |
| JP | 2007-031395 | 2/2007 |
| WO | 2005/021488 | 3/2005 |
| WO | 2005/073165 | 8/2005 |
| WO | 2007/013332 | 7/2006 |
| WO | 2006/137376 | 12/2006 |
| WO | 2006/137395 | 12/2006 |
| WO | 2007/013150 | 2/2007 |
| WO | 2007/017075 | 2/2007 |
| WO | 2007/083394 | 7/2007 |
| WO | 2008-074427 | 6/2008 |
| WO | 2008-075453 | 6/2008 |
| WO | 2008-075459 | 6/2008 |
| WO | 2008075454 | 6/2008 |
| WO | 2008075465 | 6/2008 |

OTHER PUBLICATIONS

Office Action dated Mar. 14, 2012 issued in Russian Patent Application.
European Search Report dated Dec. 11, 2012 issued in EP application No. 09806748.1.
Chinese Office Action dated Mar. 4, 2013 filed in Chinese Application No. 200980131106.2; English translation thereof.
U.S. Office Action dated Mar. 11, 2013 filed in U.S. Appl. No. 13/058,349.
Liu, Mei et al. "Recent advances in the stereoselective synthesis of β-amino acids," Terahedron, vol. 58, Issue 40, Sep. 30, 2002, pp. 7991-8035.; Cited in U.S. Office Action.
U.S. final Office Action dated Jul. 24, 2013 filed in U.S. Appl. No. 13/058,349.
Chinese Office Action dated May 9, 2014 filed in Chinese patent application No. 200980131106.2; Partial English translation.
Chinese Office Action dated Dec. 3, 2014 issued in Chinese patent application No. 200980131106.2.; Partial English translation thereof.
Xian Huang et al., "Organic Synthesis Chemistry," Chemical Industry Press, pp. 531-543, Dec. 31, 1983.; English translation thereof.
European Office Action dated Sep. 30, 2015 issued in European patent application No. 09806748.1.
Japanese Office Action dated Nov. 10, 2015 issued in Japanese patent application No. 2015-028230 and English translation thereof.

* cited by examiner

METHOD FOR PRODUCING AMIDE DERIVATIVE

TECHNICAL FIELD

The present invention relates to a method of producing an amide derivative.

BACKGROUND ART

Various amide compounds are described in International Publication (WO) No. 2005/21488 pamphlet, International Publication (WO) No. 2005/73165 pamphlet, International Publication (WO) No. 2006/137476 pamphlet, and International Publication (WO) No. 2006/137395 pamphlet.

DISCLOSURE OF INVENTION

Technical Problem

An object of the present invention is provision of a method of efficiently producing an amide derivative that exhibits excellent efficacy in terms of pest control effect.

Solution to Problem

The inventors of the present invention has made earnest study in order to develop a novel method of producing an amide derivative represented by the following Formula (3), as a result of which the inventors have found a novel production method with which the problem can be solved, and thus have achieved the invention.

Further, the inventors have also found a useful intermediate in the production the amide derivative according to the invention, and thus have achieved the invention.

Specifically, the invention is as described below.

<1>. A method of producing an amide derivative represented by the following Formula (3):

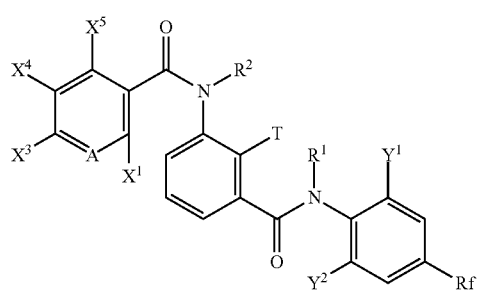

(3)

wherein, in Formula (3), $X^1$, $X^3$, $X^4$, $X^5$, A, T, $Y^1$, $Y^2$, $R^1$, $R^2$, and Rf have the same definitions as $X^1$, $X^3$, $X^4$, $X^5$, A, T, $Y^1$, $Y^2$, $R^1$, $R^2$, and Rf in Formula (1) and Formula (2) shown below, respectively, the method comprising allowing a compound represented by the following Formula (1) and a compound represented by the following Formula (2) to react with each other:

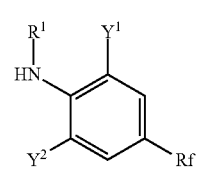

(1)

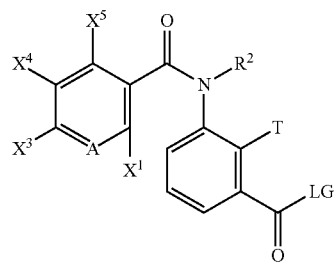

(2)

wherein, in Formula (1), $Y^1$ and $Y^2$ each independently represent a halogen atom, a $C_1$-$C_3$ haloalkyl group, or a $C_1$-$C_6$ haloalkoxy group; Rf represents a $C_3$-$C_4$ perfluoroalkyl group; and $R^1$ represents a hydrogen atom or a $C_1$-$C_4$ alkyl group, and wherein, in Formula (2), LG represents a leaving group; T represents a hydrogen atom or a fluorine atom; $R^2$ represents a hydrogen atom or a $C_1$-$C_6$ alkyl group; $X^1$, $X^3$, $X^4$, and $X^5$ each independently represent a hydrogen atom, a halogen atom, a nitro group, or a nitrile group; and A represents a nitrogen atom, or a methine group optionally substituted by a halogen atom, by a nitro group, or by a nitrile group.

<2>. The method of producing an amide derivative according to <1>, wherein, in Formula (2), the leaving group represented by LG is a halogen atom.

<3>. The method of producing an amide derivative according to <2>, wherein the amide derivative represented by Formula (3) is a compound represented by the following Formula (4):

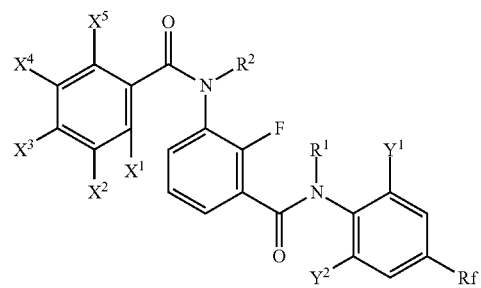

(4)

wherein, in Formula (4), $X^1$, $X^2$, $X^3$, $X^4$, and $X^5$ each independently represent a hydrogen atom, a halogen atom, a nitro group, or a nitrile group; $R^1$ represents a hydrogen atom or a $C_1$-$C_4$ alkyl group; $R^2$ represents a hydrogen atom or a $C_1$-$C_6$ alkyl group; $Y^1$ and $Y^2$ each independently represent a halogen atom, a $C_1$-$C_3$ haloalkyl group, or a $C_1$-$C_6$ haloalkoxy group; and Rf represents a $C_3$-$C_4$ perfluoroalkyl group.

<4>. The method of producing an amide derivative according to <3>, further comprising allowing a compound represented by the following Formula (5) and a compound represented by the following Formula (6) or (7) to react with each other, thereby producing a compound represented by the following Formula (8):

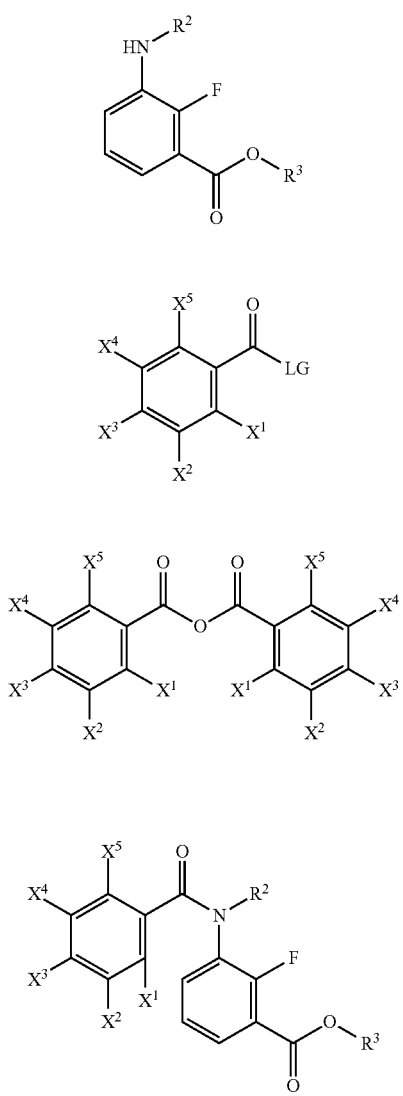

(5)

(6)

(7)

(8)

wherein, in Formula (5), $R^2$ represents a hydrogen atom or a $C_1$-$C_6$ alkyl group; and $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group;

wherein, in Formula (6), $X^1$, $X^2$, $X^3$, $X^4$, and $X^5$ each independently represent a hydrogen atom, a halogen atom, a nitro group, or a nitrile group; and LG represents a leaving group;

wherein, in Formula (7), $X^1$, $X^2$, $X^3$, $X^4$, and $X^5$ each independently represent a hydrogen atom, a halogen atom, a nitro group, or a nitrile group; and wherein, in Formula (8), $R^2$ and $R^3$ have the same definitions as $R^2$ and $R^3$ in Formula (5), respectively; and $X^1$, $X^2$, $X^3$, $X^4$, and $X^5$ have the same definitions as $X^1$, $X^2$, $X^3$, $X^4$, and $X^5$ in Formula (6) or Formula (7), respectively.

<5>. The method of producing an amide derivative according to <4>, further comprising alkylating a compound represented by Formula (8) and in which $R^2$ represents a hydrogen atom, thereby producing a compound represented by the following Formula (9):

(9)

wherein, in Formula (9), $R^{21}$ represents a $C_1$-$C_6$ alkyl group; and $R^3$, $X^1$, $X^2$, $X^3$, $X^4$, and $X^5$ have the same definitions as $R^3$, $X^1$, $X^2$, $X^3$, $X^4$, and $X^5$ in Formula (8), respectively.

<6>. The method of producing an amide derivative according to <4>, further comprising converting a compound represented by Formula (5) and in which $R^2$ represents a hydrogen atom, to a compound represented by the following Formula (10):

(10)

wherein, in Formula (10), $R^{21}$ represents a $C_1$-$C_6$ alkyl group; and $R^3$ has the same definition as $R^3$ in Formula (8).

<7>. The method of producing an amide derivative according to <4>, further comprising converting a compound represented by Formula (8) and in which $R^3$ represents a $C_1$-$C_6$ alkyl group, a $C_3$-$C_8$ cycloalkyl group, a $C_2$-$C_6$ alkenyl group, or a $C_2$-$C_6$ alkynyl group, to a compound represented by the following Formula (11):

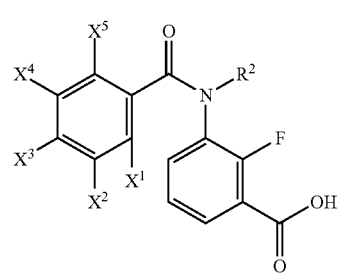

(11)

wherein, in Formula (11), $X^1$, $X^2$, $X^3$, $X^4$, $X^5$, and $R^2$ have the same definitions as $X^1$, $X^2$, $X^3$, $X^4$, $X^5$, and $R^2$ in Formula (8), respectively.

<8>. The method of producing an amide derivative according to <7>, further comprising converting the compound represented by Formula (11) to a compound represented by the following Formula (12):

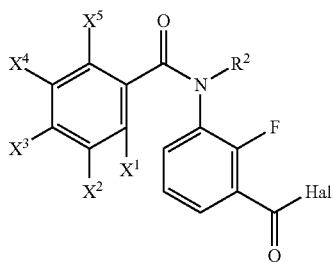

(12)

wherein, in Formula (12), $X^1$, $X^2$, $X^3$, $X^4$, $X^5$, and $R^2$ have the same definitions as $X^1$, $X^2$, $X^3$, $X^4$, $X^5$, and $R^2$ in Formula (11), respectively; and Hal represents a fluorine atom, a chlorine atom, or a bromine atom.

<9>. The method of producing an amide derivative according to <2>, wherein the amide derivative represented by Formula (3) is a compound represented by the following Formula (20):

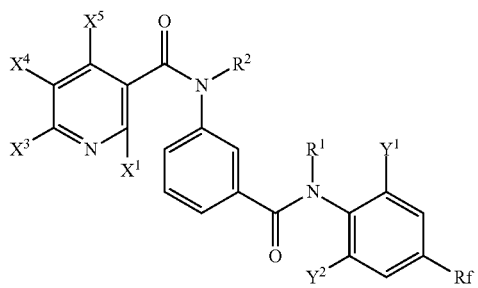

(20)

wherein, in Formula (20), $X^1$, $X^3$, $X^4$, and $X^5$ each independently represent a hydrogen atom, a halogen atom, a nitro group, or a nitrile group, provided that at least one of $X^1$ or $X^3$ represents a halogen atom; $R^1$ represents a hydrogen atom or a $C_1$-$C_4$ alkyl group; $R^2$ represents a hydrogen atom, or a $C_1$-$C_6$ alkyl group; $Y^1$ and $Y^2$ each independently represent a halogen atom, a $C_1$-$C_3$ haloalkyl group, or a $C_1$-$C_6$ haloalkoxy group; and Rf represents a $C_3$-$C_4$ perfluoroalkyl group.

<10>. A compound represented by the following Formula (8):

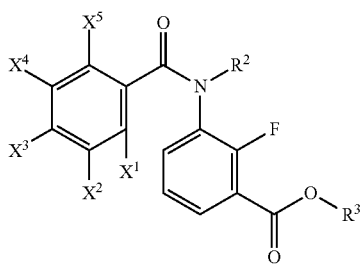

(8)

wherein, in Formula (8), $R^2$ represents a hydrogen atom or a $C_1$-$C_6$ alkyl group; $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group; and $X^1$, $X^2$, $X^3$, $X^4$, and $X^5$ each independently represent a hydrogen atom, a halogen atom, a nitro group, or a nitrile group.

<11>. A compound represented by the following Formula (12):

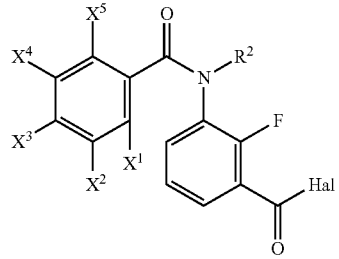

(12)

wherein, in Formula (12), $R^2$ represents a hydrogen atom or a $C_1$-$C_6$ alkyl group; Hal represents a fluorine atom, a chlorine atom, or a bromine atom; and $X^1$, $X^2$, $X^3$, $X^4$, and $X^5$ each independently represent a hydrogen atom, a halogen atom, a nitro group, or a nitrile group.

Advantageous Effects of Invention

According to the invention, a production method with which an amide derivative exhibiting excellent efficacy in terms of pest control effect can be produced with high efficiency can be provided.

BEST MODE FOR CARRYING OUT THE INVENTION

The terms used in connection with the Formulae according to the invention respectively have the definitions described below.

"Halogen atom" represents a fluorine atom, a chlorine atom, a bromine atom, or an iodine atom.

In regard to the expression "$C_a$-$C_b$ (wherein a and b represent integers of 1 or greater)", for example, "$C_1$-$C_3$" means that the number of carbon atoms is from 1 to 3, and "$C_2$-$C_6$" means that the number of carbon atoms is from 2 to 6.

"n-" means normal, "i-" means iso, "s-" means secondary, and "t-" means tertiary.

"$C_1$-$C_3$ haloalkyl group" represents a linear or branched alkyl group having from 1 to 3 carbon atoms, and substituted by one or more halogen atoms that may be the same as or different from each other, such as monofluoromethyl, difluoromethyl, trifluoromethyl, monochloromethyl, dichloromethyl, trichloromethyl, monobromomethyl, dibromomethyl, tribromomethyl, pentafluoroethyl, heptafluoro-n-propyl, heptafluoro-i-propyl, 2,2-difluoroethyl, 2,2-dichloroethyl, 2,2,2-trifluoroethyl, 1-fluoroethyl, 2-fluoroethyl, 1-chloroethyl, 2-chloroethyl, 1-bromoethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-chloro-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, or 3-bromo-n-propyl.

"$C_1$-$C_6$ haloalkoxy group" represents a linear or branched alkyloxy group having from 1 to 6 carbon atoms and substituted by one or more halogen atoms that may be the same as or different from each other, such as trifluoromethyloxy, pentafluoroethyloxy, heptafluoro-n-propyloxy, heptafluoro-i-propyloxy, 2,2-difluoroethyloxy, 2,2-dichloroethyloxy, 2,2,2-trifluoroethyloxy, 2-fluoroethyloxy, 2-chloroethyloxy, 2-bromoethyloxy, 2-iodoethyloxy, 2,2,2-trichloroethyloxy, 2,2,2-tribromoethyloxy, 1,3-difluoro-2-propyloxy, 1,3-dichloro-2-propyloxy, 1-chloro-3-fluoro-2-propyloxy, 1,1,1-trifluoro-2-propyloxy, 2,3,3,3-trifluoro-n-propyloxy, 4,4,4-trifluoro-n-butyloxy, 1,1,1,3,3,3-hexafluoro-2-propyloxy, 1,1,1,3,3,3-hexafluoro-2-chloro-2-propyloxy, 1,1,1,3,3,3-hexafluoro-2-bromo-2-propyloxy, 1,1,2,3,3,3-hexafluoro-2-bromo-n-propyloxy, 1,1,2,3,3,3-hexafluoro-1-bromo-2-propyloxy, 2,2,3,3,3-pentafluoro-n-propyloxy, 3-fluoro-n-propyloxy, 3-chloro-n-propyloxy, 3-fluoro-n-propyloxy, 3-chloro-n-propyloxy, 3-bromo-n-propyloxy, 3,3,4,4,4-pentafluoro-2-butyloxy, nonafluoro-n-butyloxy, nonafluoro-2-butyloxy, 5,5,5-trifluoro-n-pentyloxy, 4,4,5,5,5-pentafluoro-2-pentyloxy, 3-chloro-n-pentyloxy, or 4-bromo-2-pentyloxy.

"$C_1$-$C_4$ alkyl group" represents a linear or branched alkyl group having from 1 to 4 carbon atoms such as methyl, ethyl, n-propyl, i-propyl, n-butyl, i-butyl, s-butyl, or t-butyl.

"$C_1$-$C_6$ alkyl group" represents a linear or branched alkyl group having from 1 to 6 carbon atoms such as methyl, ethyl, n-propyl, i-propyl, n-butyl, i-butyl, s-butyl, t-butyl, n-pentyl, i-pentyl, neopentyl, 4-methyl-2-pentyl, n-hexyl, or 3-methyl-n-pentyl.

"$C_3$-$C_8$ cycloalkyl group" represents an alkyl group having from 3 to 8 carbon atoms and having a cyclic structure, such as cyclopropyl, cyclobutyl, cyclopentyl, 2-methylcyclopentyl, 3-methylcyclopentyl, cyclohexyl, 2-methylcyclohexyl, 3-methylcyclohexyl, or 4-methylcyclohexyl.

"$C_2$-$C_6$ alkenyl group" represents a linear or branched alkenyl group having from 2 to 6 carbon atoms and having a double bond in its carbon chain, such as vinyl, 1-propenyl, allyl, isopropenyl, 1-butenyl, 2-butenyl, 3-butenyl, 1,3-butadienyl, or 1-hexenyl.

"$C_2$-$C_6$ alkynyl group" represents a linear or branched alkynyl group having from 2 to 6 carbon atoms and having a triple bond in its carbon chain, such as ethynyl, propargyl, 2-pentynyl, 1-butyn-3-yl, 1-butyn-3-methyl-3-yl, or 3-hexynyl.

"$C_3$-$C_4$ perfluoroalkyl group" represents a linear or branched alkyl group having from 3 to 4 carbon atoms and of which all hydrogen atoms have been replaced with fluorine atoms, such as perfluoro-n-propyl, perfluoro-i-propyl, perfluoro-n-butyl, perfluoro-i-butyl, perfluoro-s-butyl, or perfluoro-t-butyl.

Each of the $C_1$-$C_6$ alkyl group, $C_3$-$C_8$ cycloalkyl group, $C_2$-$C_6$ alkenyl group, and $C_2$-$C_6$ alkynyl group that $R^3$ may represent may have a substituent, and examples of the substituent include at least one substituent selected from an unsubstituted linear or branched alkyl group having from 1 to 6 carbon atoms, an unsubstituted cyclic cycloalkyl group having from 3 to 8 carbon atoms, an unsubstituted linear, branched, or cyclic alkenyl group having from 2 to 6 carbon atoms, an unsubstituted linear, branched, or cyclic alkynyl group having from 2 to 6 carbon atoms, a halogen atom, a phenyl group, an amino group, a cyano group, a nitro group, a hydroxy group, an alkyloxy group, a benzyloxy group, an alkylthio group, a carboxy group, a benzyl group, a heterocyclic group, a phenylsulfonyl group, a phenylcarbonyl group, and a phenylamino group. When there are two or more substituents, the substituents may be the same as each other or different from each other.

The substituent may itself has a further substituent, if possible. Specific examples of the further substituent are the same as the above.

Specific examples of the $C_1$-$C_6$ alkyl group, $C_3$-$C_8$ cycloalkyl group, $C_2$-$C_6$ alkenyl group, and $C_2$-$C_6$ alkynyl group when these groups have substituents include a methoxymethyl group, a benzyloxymethyl group, a phenacyl group, a p-bromophenacyl group, a p-methoxyphenacyl group, a 2-(p-toluenesulfonyl)ethyl group, a trichloroethyl group, a 2-chloroethyl group, a 2-methylthioethyl group, a 1-methyl-1-phenylethyl group, a cinnamyl group, a p-methylthiophenyl group, a benzyl group, a 2,4,6-trimethylbenzyl group, a cinnamyl group, a p-bromobenzyl group, a o-nitrobenzyl group, a p-nitrobenzyl group, a p-methoxybenzyl group, a p-methylthiophenyl group, a 4-picolyl group, and a piperonyl group.

Some of the compounds represented by the Formula (3) according to the invention include one or plural chiral carbon atoms or chiral centers in their structures, and thus there may be two or more optical isomers. The scope of the invention encompasses the individual optical isomers and any mixture containing such optical isomers at an arbitrary ratio.

Further, some of the compounds represented by the Formula (3) according to the invention include two or more kinds of geometrical isomer derived from carbon-carbon double bond(s) in their structural formulae. The scope of the invention also encompasses any mixture containing such geometrical isomers at an arbitrary ratio.

The method of producing an amide derivative according to the invention, and a compound as a production intermediate that can be suitably used in the production method and a method of producing the compound are described below. However, the invention is not limited thereto.

The method of producing an amide derivative represented by the following Formula (3) according to the invention includes a process of allowing a compound represented by the following Formula (1) and a compound represented by the following Formula (2) to react with each other. The production method enables efficient production of an amide derivative that exhibits excellent efficacy in terms of pest control effect.

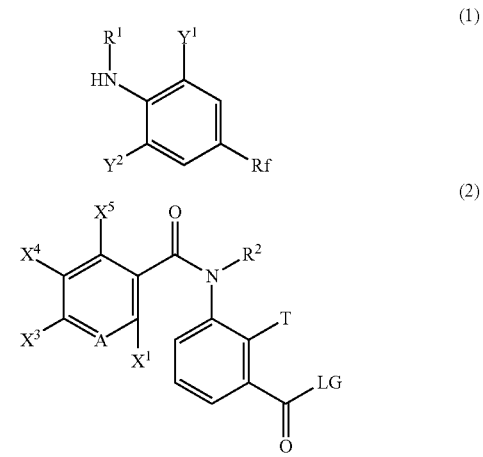

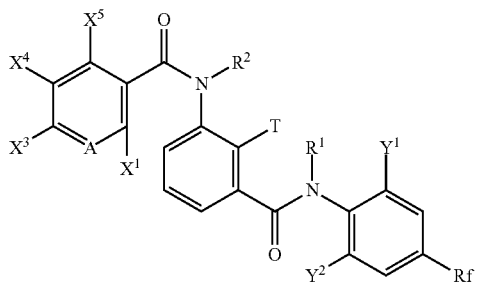

(3)

In Formula (1) to Formula (3), $Y^1$ and $Y^2$ each independently represent a halogen atom, a $C_1$-$C_3$ haloalkyl group, or a $C_1$-$C_6$ haloalkoxy group; Rf represents a $C_3$-$C_4$ perfluoroalkyl group; $R^1$ represents a hydrogen atom or a $C_1$-$C_4$ alkyl group; LG represents a leaving group; T represents a hydrogen atom or a fluorine atom; $R^2$ represents a hydrogen atom or a $C_1$-$C_6$ alkyl group; $X^1$, $X^3$, $X^4$, and $X^5$ each independently represent a hydrogen atom, a halogen atom, a nitro group, or a nitrile group; and A represents a nitrogen atom, or a methine group which may be substituted by a halogen atom, a nitro group, or a nitrile group.

Examples of the leaving group represented by LG include a halogen atom, a hydroxyl group, an aryloxy group, and an acyloxy group; from the viewpoint of production efficiency, the leaving group is preferably a halogen atom, an aryloxy group, or an acyloxy group, and more preferably a halogen atom.

According to the invention, as the conditions for allowing the compound represented by Formula (1) and the compound represented by Formula (2) to react with each other, commonly-used reaction conditions can be employed without particular limitations.

For example, an amide derivative represented by Formula (3) can be produced by allowing an aromatic carboxylic acid derivative having a leaving group (LG) shown in Formula (2) and an aromatic amine derivative represented by Formula (1) to react with each other in an appropriate solvent or in the absence of solvent. In the present process, an appropriate base may also be used.

The solvent may be any solvent that does not considerably inhibit the progress of the reaction, and may be an inert solvent, examples of which include: water; aromatic hydrocarbons such as benzene, toluene, xylene, chlorobenzene, and dichlorobenzene; halogenated hydrocarbons such as dichloromethane, chloroform, and carbon tetrachloride; chain ethers or cyclic ethers such as diethyl ether, dioxane, tetrahydrofuran, and 1,2-dimethoxyethane; esters such as ethyl acetate and butyl acetate; alcohols such as methanol and ethanol; ketones such as acetone, methyl isobutyl ketone, and cyclohexanone; nitriles such as acetonitrile and propionitrile; and aprotic polar solvents such as 1,3-dimethyl-2-imidazolidinone, sulfolane, dimethyl sulfoxide, N,N-dimethylformamide, N-methylpyrrolidone, N,N-dimethylacetamide, and hexamethylphosphoric amide. These solvents may be used singly, or in mixture of two or more thereof.

Examples of the base include: organic bases such as trimethylamine, triethylamine, tri-n-butylamine, piperidine, pyridine, 2-picoline, 3-picoline, 2,6-lutidine, N-methylmorpholine, N,N-diethylaniline, N-ethyl-N-methylaniline, diisopropylethylamine, 3-methylimidazole, 1,8-diazabicyclo[5.4.0]-7-undecene, 1,4-diazabicyclo[2.2.2]octane, and 4-dimethylaminopyridine; alkali metal hydroxides such as lithium hydroxide, sodium hydroxide, and potassium hydroxide; carbonates such as sodium hydrogen carbonate, sodium carbonate, and potassium carbonate; phosphates such as dipotassium monohydrogen phosphate and trisodium phosphate; alkali metal hydrides such as sodium hydride; alkali metal alcoholates such as sodium methoxide and sodium ethoxide; and lithium amides such as lithium diisopropylamide.

These bases may be appropriately selected and may be used in an amount that is from 0.01 to 5 molar equivalents relative to the compound represented by Formula (2).

The reaction temperature may be appropriately selected within the range of from −20° C. to the reflux temperature of the solvent to be used, and the reaction time may be appropriately selected within the range of from several minutes to 96 hours.

An aromatic carboxyl halide which is a compound represented by Formula (2) and in which LG represents a halogen atom can be produced from an aromatic carboxylic acid which is represented by Formula (2) and in which LG is a hydroxyl group, using an equimolar or greater amount of halogenating agent.

Examples of the halogenating agent include thionyl chloride, thionyl bromide, oxalyl chloride, phosphorus oxychloride, oxalyl chloride, phosphorus trichloride, and phosphorus pentachloride.

This reaction may be carried out using a solvent, in which case any inert solvent may be used. One solvent, or two or more solvents, may be appropriately selected from the following: chain ethers or cyclic ethers such as diethyl ether, t-butyl ethyl ether, tetrahydrofuran, dioxane, and 1,2-dimethoxyethane; halogenated hydrocarbons such as methylene chloride, chloroform, carbon tetrachloride, dichloroethane, trichloroethane, dichloroethylene, chlorobenzene, and dichlorobenzene; aromatic hydrocarbons such as benzene, toluene, xylene, chlorobenzene, and dichlorobenzene; aliphatic hydrocarbons such as n-hexane, heptane, octane, and cyclohexane; esters such as ethyl acetate and butyl acetate; nitriles such as acetonitrile and propionitrile; and aprotic polar solvents such as N,N-dimethylformamide, N,N-dimethylacetamide, dimethyl sulfoxide, N-methylpyrrolidone, 1,3-dimethyl-2-imidazolidinone; and the like.

The reaction may be usually carried out at −20° C. to 140° C., and the reaction time is usually selected, as appropriate, within the range of from 0.1 hours to 96 hours.

It is also possible to produce an amide derivative represented by Formula (3) from a compound represented by Formula (1) and a compound which is represented by Formula (2) and in which LG represents a hydroxyl group, without using a halogenating agent. An example of the method is a method of using a condensing agent, which uses N,N'-dicyclohexylcarbodiimide, and optionally also using an additive such as 1-hydroxybenzotriazole or 1-hydroxysuccinimide, as in a method described in Chem. Ber. page 788 (1970). Other examples of the condensing agent that can be used in this method include 1-ethyl-3-(3-dimethylaminopropyl)carbodiimide, and 1,1'-carbonylbis-1H-imidazole.

Another method for producing an amide derivative represented by Formula (3) from a compound represented by Formula (1) and a compound which is represented by Formula (2) and in which LG represents a hydroxyl group is a mixed anhydride method using a chloroformate; specifically, an amide derivative represented by Formula (3) can be produced according to a method described in J. Am. Chem. Soc., p. 5012, (1967). Examples of the chloroformate that can be used in this method include isobutyl chloroformate and isopropyl chloroformate. Other examples than chloroformates include diethylacetyl chloride and trimethylacetyl chloride.

Still another method for producing an amide derivative represented by Formula (3) from a compound represented by Formula (1) and a compound which is represented by Formula (2) and in which LG represents a hydroxyl group is an active ester method using an aryloxy group as a leaving group. Specifically, an amide derivative represented by Formula (3) can be produced from a phenol derivative and a compound which is represented by Formula (2) and in which LG represents a hydroxyl group, using a condensing agent such as N,N'-dicyclohexylcarbodiimide, 1-ethyl-3-(3-dimethylaminopropyl)carbodiimide, or 1,1'-carbonylbis-1H-imidazole, and optionally using an additive such as 1-hydroxybenzotriazole or 1-hydroxysuccinimide. Examples of the aryloxy group used in the active ester method include a p-nitrophenyloxy group, a 2,4-dinitrophenyloxy group, a pentafluorophenyloxy group, a 1,3,5-trichlorophenyloxy group, and a pentachlorophenyloxy group.

Each of the method of using a condensing agent, the mixed anhydride method, and the active ester method is not limited to be conducted with the solvent, reaction temperature, and reaction time described in the above documents. An inert solvent that does not considerably inhibit the progress of the reaction may be used as appropriate. Similarly, the reaction temperature and the reaction time may also be selected as appropriate, in accordance with the progress of the reaction.

The amide derivative represented by Formula (3) according to the invention thus obtained may be isolated from the reaction mixture after completion of the reaction, by employing a common separation formation means, such as extraction, concentration, neutralization, filtration, recrystallization, column chromatography, or distillation. The target substance may alternatively be supplied to a next reaction process without being isolated from the reaction system.

A compound represented by the following Formula (22), which is a compound represented by Formula (2) wherein LG represents a hydroxyl group, can be produced in the manner described below.

From among compounds represented by the following Formula (21), a compound in which $R^3$ represents a $C_1$-$C_6$ alkyl group, a $C_3$-$C_8$ cycloalkyl group, a $C_2$-$C_6$ alkenyl group, or a $C_2$-$C_6$ alkynyl group can be converted to a compound represented by the following Formula (22) by hydrolysis utilizing a common technique, or by a method using a Pd catalyst. Specifically, a compound represented by Formula (22) can be obtained from a compound represented by Formula (21) in a manner similar to the below-described method of producing a compound represented by Formula (11) from a compound represented by Formula (8).

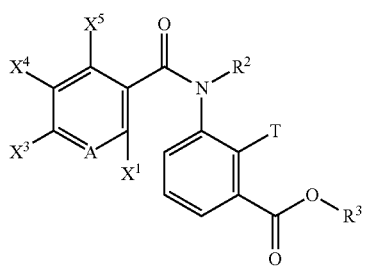

(21)

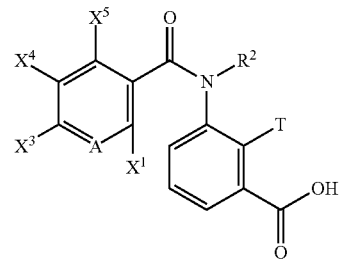

(22)

In Formula (21) and Formula (22), $X^1$, $X^3$, $X^4$, $X^5$, T, A, and $R^2$ have the same definitions as $X^1$, $X^3$, $X^4$, $X^5$, T, A, and $R^2$ in Formula (3), respectively; and $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group.

Further, the compound represented by Formula (22) can be converted to a compound which is represented by Formula (2) and in which LG represents a halogen atom by a known method using a halogenating agent. Specifically, a compound which is represented by Formula (2) and in which LG represents a halogen atom can be obtained from the compound represented by Formula (22) in a manner similar to the below-described method of producing a compound represented by Formula (12) from a compound represented by Formula (11).

The compound represented by Formula (21) can be produced by allowing a compound represented by the following Formula (23), and a compound represented by the following Formula (24) or a compound represented by the following Formula (25) to react with each other.

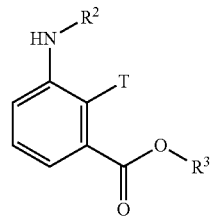

(23)

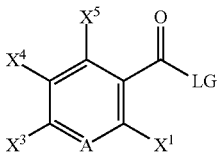

(24)

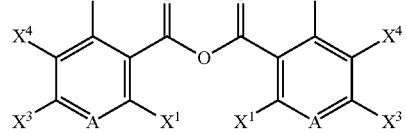

(25)

In Formula (23) to Formula (25), $X^1$, $X^3$, $X^4$, $X^5$, T, A, and $R^2$ have the same definitions as $X^1$, $X^3$, $X^4$, $X^5$, T, A, and $R^2$ in Formula (3), respectively; $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group; and LG represents a leaving group.

Examples of the leaving group represented by LG include a halogen atom, a hydroxyl group, and an aryloxy group; the leaving group is preferably a halogen atom from the viewpoint of production efficiency.

Specifically, the method of allowing the compound represented by Formula (23), and the compound represented by Formula (24) or the compound represented by Formula (25) to react with each other can be carried out in a manner similar to the below-described method of allowing a compound represented by Formula (5), and a compound represented by Formula (6) or a compound represented by Formula (7) to react with each other.

A compound represented by the following Formula (26), which is a compound represented by Formula (21) wherein $R^2$ represents a $C_1$-$C_6$ alkyl group, can be produced by alkylating a compound represented by the following Formula (27). Specifically, a compound represented by the following Formula (26) can be produced in a manner similar to the below-described method of producing a compound represented by Formula (9) from a compound represented by Formula (13).

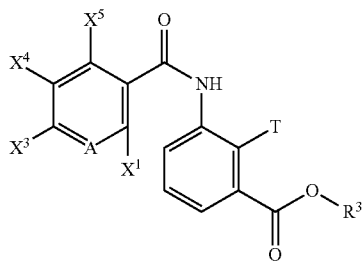

(27)

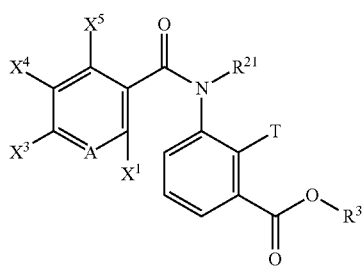

(26)

In Formula (26) and Formula (27), $X^1$, $X^3$, $X^4$, $X^5$, T, and A have the same definitions as $X^1$, $X^3$, $X^4$, $X^5$, T, and A in Formula (3), respectively; $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group; and $R^{21}$ represents a $C_1$-$C_6$ alkyl group.

The compound represented by Formula (26) can alternatively be produced by allowing a compound represented by the following Formula (28) as the compound represented by Formula (23), and the compound represented by Formula (24) or the compound represented by Formula (25) to react with each other.

A compound represented by the following Formula (28) can be produced by alkylating a compound represented by the following Formula (29).

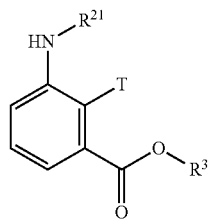

(28)

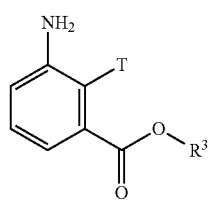

(29)

In Formula (28) and Formula (29), $R^3$ and $R^{21}$ have the same definitions as $R^3$ and $R^{21}$ in Formula (26), respectively.

The method of producing a compound represented by Formula (28) from a compound represented by Formula (29) can be carried out in a manner similar to the below-described method of producing a compound represented by Formula (10) from a compound represented by Formula (14).

In the invention, the amide derivative represented by Formula (3) is preferably a compound represented by the following Formula (4) or a compound represented by the following Formula (20), from the viewpoints of pest control activity.

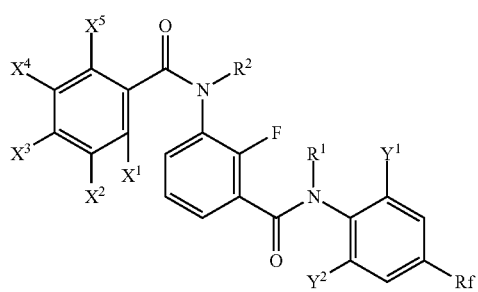

(4)

In Formula (4), $X^1$, $X^2$, $X^3$, $X^4$, and $X^5$ each independently represent a hydrogen atom, a halogen atom, a nitro group, or a nitrile group; $R^1$ represents a hydrogen atom or a $C_1$-$C_4$ alkyl group; $R^2$ represents a hydrogen atom or a $C_1$-$C_6$ alkyl group; $Y^1$ and $Y^2$ each independently represent a halogen atom, a $C_1$-$C_3$ haloalkyl group, or a $C_1$-$C_6$ haloalkoxy group; and Rf represents a $C_3$-$C_4$ perfluoroalkyl group.

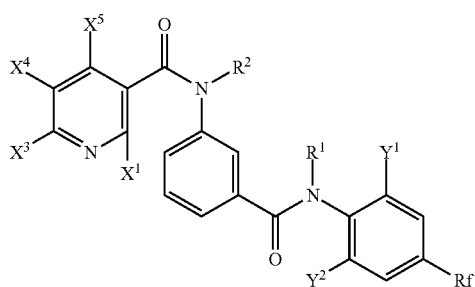

(20)

In Formula (20), $X^1$, $X^3$, $X^4$, and $X^5$ each independently represent a hydrogen atom, a halogen atom, a nitro group, or a nitrile group, provided that at least one of $X^1$ or $X^3$ represents a halogen atom; $R^1$ represents a hydrogen atom or a $C_1$-$C_4$ alkyl group; $R^2$ represents a hydrogen atom or a $C_1$-$C_6$ alkyl group; $Y^1$ and $Y^2$ each independently represent a halogen atom, a $C_1$-$C_3$ haloalkyl group, or a $C_1$-$C_6$ haloalkoxy group; and Rf represents a $C_3$-$C_4$ perfluoroalkyl group.

In the invention, the amide compound represented by Formula (4) can be produced in a manner similar to the production of the amide derivative represented by Formula (3). In the invention, the method of producing an amide compound represented by Formula (4) preferably further includes a process of producing a compound represented by the following Formula (8) by allowing a compound represented by the following Formula (5), and a compound represented by the following Formula (6) or a compound represented by the following Formula (7) to react with each other.

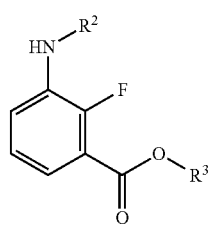

(5)

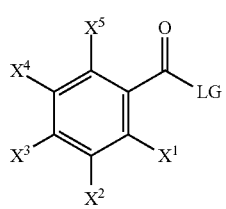

(6)

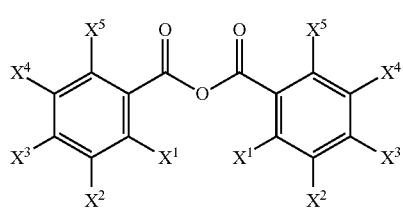

(7)

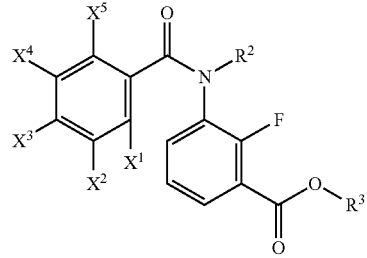

(8)

In Formula (5) to Formula (8), $X^1$, $X^2$, $X^3$, $X^4$, $X^5$, and $R^2$ have the same definitions as $X^1$, $X^2$, $X^3$, $X^4$, $X^5$, and $R^2$ in Formula (4), respectively; $R^3$ represents a hydrogen atom, a $C_1$-$C_6$ alkyl group, a $C_3$-$C_8$ cycloalkyl group, a $C_2$-$C_6$ alkenyl group, or a $C_2$-$C_6$ alkynyl group; and LG represents a leaving group.

Examples of the leaving group represented by LG include a halogen atom, a hydroxyl group, an aryloxy group, and an acyloxy group. From the viewpoint of production efficiency, the leaving group is preferably a halogen atom, an aryloxy group, or an acyloxy group, and more preferably a halogen atom.

The compound represented by Formula (8) can be produced by allowing a compound represented by Formula (5), and an aromatic carboxylic acid derivative represented by Formula (6) or Formula (7) to react with each other in an appropriate solvent or in the absence of solvent. In the present process, an appropriate base or solvent may be used.

The solvent to be used may be any solvent that does not considerably inhibit the progress of the reaction, and examples thereof include: aromatic hydrocarbons such as benzene, toluene, and xylene; halogenated carbons such as methylene chloride, chloroform, and carbon tetrachloride; chain ethers or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; aprotic polar solvents such as N,N-dimethylformamide, N,N-dimethylacetamide, N-methylpyrrolidone, hexamethylphosphoric triamide, dimethyl sulfoxide, and 1,3-dimethyl-2-imidazolidinone; nitriles such as acetonitrile and propionitrile; and water. These solvents may be used singly, or a mixture of two or more of these solvents may be used.

Further, examples of the base include: organic bases such as trimethylamine, triethylamine, tri-n-butylamine, piperidine, pyridine, 2-picoline, 3-picoline, 2,6-lutidine, diisopropylethylamine, and 4-dimethylaminopyridine; alkali metal hydroxides such as lithium hydroxide, sodium hydroxide, and potassium hydroxide; carbonates such as sodium hydrogen carbonate, sodium carbonate, and potassium carbonate; phosphates such as dipotassium monohydrogen phosphate, and trisodium phosphate; alkali metal hydrides such as sodium hydride; alkali metal alcoholates such as sodium methoxide and sodium ethoxide; and lithium amides such as lithium diisopropylamide.

The base may be appropriately selected from these bases, and may be used in an amount of from 0.01 to 5 molar equivalents relative to the compound represented by Formula (5).

The reaction temperature may be appropriately selected within the range of from −20° C. to the reflux temperature of the solvent to be used. The reaction time may be appropriately selected within the range of from several minutes to 96 hours.

An aromatic carboxyl halide compound which is represented by Formula (6) and in which LG represents a halogen atom can be easily produced from an aromatic carboxylic acid by a common method using a halogenating agent. Examples of the halogenating agent include thionyl chloride, oxalyl chloride, phosgene, phosphorus oxychloride, phosphorus pentachloride, phosphorus trichloride, thionyl bromide, and phosphorus tribromide.

An aromatic carboxyl anhydride represented by Formula (7) can be produced from an aromatic carboxylic acid in the co-presence of a dehydrating agent. Examples of the dehydrating agent include: acid anhydrides or acid chlorides, such as phosphoryl chloride, acetic anhydride, and trifluoroacetic anhydride; haloformic esters, and carbodiimides.

A compound represented by Formula (8) can be produced, without using a halogenating agent, from an aromatic carboxylic acid which is represented by Formula (6) and in which LG represents a hydroxyl group and an aniline derivative. Regarding the method, for example, a method described in Chem. Bet, p. 788 (1970) may be employed. Specifically, a method of using a condensing agent, which uses N,N'-dicyclohexylcarbodiimide, and optionally also using an additive such as 1-hydroxybenzotriazole or 1-hydroxysuccinimide, may be employed. In regard to other examples of the condensing agent to be used in this method, a peptide condensation reagent such as 1-ethyl-3-(3-dimethylaminopropyl)carbodiimide, N,N'-carbonylbis-1H-imidazole, diphenylphosphoric acid azide, or diethyl cyanophosphate may be used singly. The reaction temperature is usually −20° C. to +50° C., and preferably 0° C. to room temperature. Examples of commonly used solvents include dioxane, N,N-dimethylformamide, dimethyl sulfoxide, chloroform, methylene chloride, and tetrahydrofuran, which may be used singly or in mixture.

Another example of the method is a mixed anhydride method using a chloroformate. For example, a method described in J. Am. Chem. Soc., p. 5012 (1967) may be employed. Examples of the chloroformate to be used in this method include methyl chloroformate, propyl chloroformate, and i-butyl chloroformate. Other examples than chloroformates include diethylacetyl chloride and trimethylacetyl chloride.

Each of the method of using a condensing agent and the mixed anhydride method is not limited to be conducted with the solvents, the reaction temperature, and the reaction time described in the above documents. An inert solvent that does not considerably inhibit the progress of reaction may be used as appropriate. The reaction temperature and the reaction time may also be selected as appropriate, in accordance with the progress of the reaction.

The method of producing a compound represented by Formula (4) preferably further includes a process of obtaining a compound represented by the following Formula (9) by alkylating a compound represented by the following Formula (13), which is a compound represented by Formula (8) wherein $R^2$ represents a hydrogen atom.

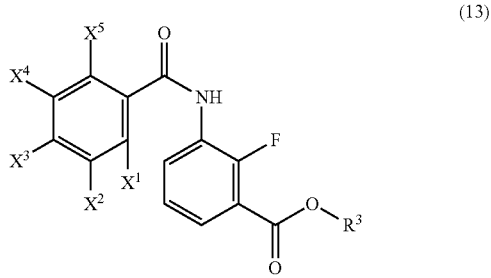

(13)

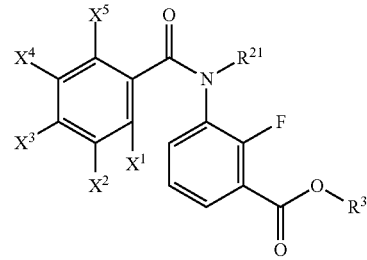

(9)

In Formula (9) and Formula (13), $X^1$, $X^2$, $X^3$, $X^4$, $X^5$, and $R^3$ have the same definitions as $X^1$, $X^2$, $X^3$, $X^4$, $X^5$, and $R^3$ in Formula (8), respectively; and $R^{21}$ represents a $C_1$-$C_6$ alkyl group.

The compound represented by Formula (9) can be produced by allowing a compound represented by Formula (13) to react with a predetermined reactive agent (preferably, an alkylating agent), using a base in a solvent.

The solvent may be any solvent that does not considerably inhibit the progress of the reaction, and examples thereof include: aliphatic hydrocarbons such as n-hexane, cyclohexane, and methylcyclohexane; aromatic hydrocarbons such as benzene, toluene, and xylene; halogenated carbons such as methylene chloride, chloroform, and 1,2-dichloroethane; chain ethers or cyclic ethers such as diethyl ether, dioxane, tetrahydrofuran, and 1,2-dimethoxyethane; esters such as ethyl acetate and butyl acetate; ketones such as acetone, methyl isobutyl ketone, and cyclohexanone; aprotic polar solvents such as N,N-dimethylformamide, N,N-dimethylacetamide, N-methylpyrrolidone, hexamethylphosphoric triamide, dimethyl sulfoxide, and 1,3-dimethyl-2-imidazolidinone; nitriles such as acetonitrile and propionitrile; and alcohols such as methanol and ethanol. These solvents may be used singly, or a mixture of two or more these solvents may be used.

Examples of the base include: organic bases such as triethylamine, tri-n-butylamine, piperidine, pyridine, and 4-dimethylaminopyridine; alkali metal hydroxides such as lithium hydroxide, sodium hydroxide, and potassium hydroxide; carbonates such as sodium hydrogen carbonate, sodium carbonate, and potassium carbonate; phosphates such as dipotassium monohydrogen phosphate, and trisodium phosphate; alkali metal hydrides such as sodium hydride; alkali metal alcoholates such as sodium methoxide, and sodium ethoxide; organolithium such as n-butyllithium; Grignard reagents such as ethylmagnesium bromide; and lithium amides such as lithium diisopropylamide.

The base may be used in an amount of from 0.01 to 5 molar equivalents relative to the compound represented by Formula (13). The base may be appropriately selected from the above bases, or the base may be used as a solvent.

Examples of the reactive agent that can be used include: alkyl halides such as methyl iodide, ethyl bromide, ethyl iodide, trifluoromethyl iodide, n-propyl iodide, and 2,2,2-trifluoroethyl iodide; allyl halides such as allyl iodide; propargyl halides such as propargyl bromide; acyl halides such as acetyl chloride; acid anhydrides such as trifluoroacetic anhydride; and alkylsulfuric acids such as dimethylsulfuric acid and diethylsulfuric acid.

The reactive agent may be used in an amount of from 1 to 5 molar equivalents relative to the compound represented by Formula (13). The reactive agent may be appropriately selected from the above reactive agents, or may be used as a solvent.

The reaction temperature may be appropriately selected within the range of from −80° C. to the reflux temperature of the solvent to be used, and the reaction time may be appropriately selected within the range of from several minutes to 96 hours.

The method of producing a compound represented by Formula (4) preferably further includes a process of obtaining a compound represented by the following Formula (10) by alkylating a compound represented by the following Formula (14), which is a compound represented by Formula (5) wherein $R^2$ represents a hydrogen atom.

The compound represented by Formula (9) can be produced by allowing a compound represented by the following Formula (10), which is used as a compound represented by Formula (5), to react with a compound represented by Formula (6) or a compound represented by Formula (7).

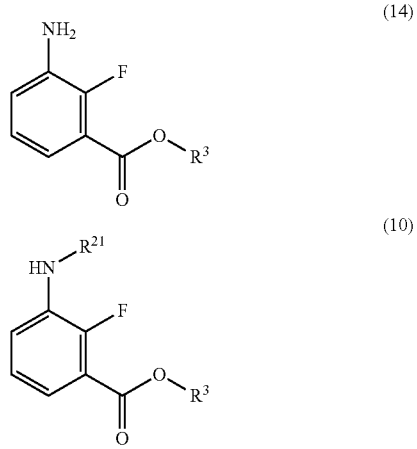

In Formula (10) and Formula (14), $R^3$ and $R^{21}$ have the same definitions as $R^3$ and $R^{21}$ in Formula (9), respectively.

Examples of the method of producing a compound represented by Formula (10) from a compound represented by Formula (14) include the following method A to method C.

(Method A)

An alkylated compound represented by Formula (10) can be produced by allowing a compound represented by Formula (14), which has an amino group, to react with an aldehyde or a ketone in a solvent, adding a catalyst, and allowing the reaction to proceed in a hydrogen atmosphere.

The solvent may be any solvent that does not considerably inhibit the progress of the reaction, and examples of the solvent include: aliphatic hydrocarbons such as n-hexane, cyclohexane, and methylcyclohexane; aromatic hydrocarbons such as benzene, xylene, and toluene; halogenated hydrocarbons such as methylene chloride, chloroform, carbon tetrachloride, and 1,2-dichloroethane; chain ethers or cyclic ethers such as diethyl ether, dioxane, tetrahydrofuran, and 1,2-dimethoxyethane; aprotic polar solvents such as N,N-dimethylformamide, N,N-dimethylacetamide, N-methylpyrrolidone, 1,3-dimethyl-2-imidazolidinone, sulfolane, dimethyl sulfoxide, and hexamethylphosphoric triamide; nitriles such as acetonitrile and propionitrile; esters such as ethyl acetate and butyl acetate; alcohols such as methanol and ethanol; and water. These solvents may be used singly, or in mixture of two or more thereof.

Examples of the catalyst include: palladium catalysts such as palladium/carbon, and palladium hydroxide/carbon; nickel catalysts such as Raney nickel; cobalt catalysts, platinum catalysts; ruthenium catalysts; and rhodium catalysts.

Examples of the aldehyde include aldehydes such as formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, and bromoacetaldehyde.

Examples of the ketone include ketones such as acetone, perfluoroacetone, and methyl ethyl ketone.

The reaction pressure may be appropriately selected within the range of from 1 atmosphere to 100 atmospheres. The reaction temperature may be appropriately selected within the range of from −20° C. to the reflux temperature of the solvent to be used. Further, the reaction time may be appropriately selected within the range of from several minutes to 96 hours.

(Method B)

The compound represented by Formula (10) can be produced by allowing a compound represented by Formula (14) to react with an aldehyde or a ketone in a solvent, and treating the resultant with a reducing agent.

The solvent may be any solvent that does not considerably inhibit the progress of the reaction, and examples of the solvent include: aliphatic hydrocarbons such as n-hexane, cyclohexane, and methylcyclohexane; aromatic hydrocarbons such as benzene, xylene, and toluene; halogenated hydrocarbons such as dichloromethane, chloroform, carbon tetrachloride, and 1,2-dichloroethane; chain ethers or cyclic ethers such as diethyl ether, dioxane, tetrahydrofuran, and 1,2-dimethoxyethane; aprotic polar solvents such as N,N-dimethylformamide, N,N-dimethylacetamide, N-methylpyrrolidone, 1,3-dimethyl-2-imidazolidinone, sulfolane, dimethyl sulfoxide, and hexamethylphosphoric triamide; nitriles such as acetonitrile, and propionitrile; esters such as ethyl acetate and butyl acetate; alcohols such as methanol and ethanol; and water. These solvents may be used singly, or in mixture of two or more thereof.

Examples of the reducing agent include borohydrides such as sodium borohydride, sodium cyanoborohydride, and sodium triacetate borohydride.

Examples of the aldehyde include aldehydes such as formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, and bromoacetaldehyde.

Examples of the ketone include ketones such as acetone, perfluoroacetone, and methyl ethyl ketone.

The reaction temperature may be appropriately selected within the range of from −20° C. to the reflux temperature of the solvent to be used. Further, the reaction time may be appropriately selected with in the range of from several minutes to 96 hours.

(Method C)

A compound represented by Formula (10) can be produced by allowing the compound represented by Formula (14) to react with an aldehyde in a solvent or in the absence of solvent.

The solvent may be any solvent that does not considerably inhibit the progress of the reaction, and examples of the solvent include: aliphatic hydrocarbons such as n-hexane, cyclohexane, and methylcyclohexane; aromatic hydrocarbons such as benzene, xylene, and toluene; halogenated hydrocarbons such as dichloromethane, chloroform, carbon tetrachloride, and 1,2-dichloroethane; chain ethers or cyclic ethers such as diethyl ether, dioxane, tetrahydrofuran, and 1,2-dimethoxyethane; aprotic polar solvents such as N,N- dimethylformamide, N,N-dimethylacetamide, N-methylpyrrolidone, hexamethylphosphoric triamide, 1,3-dimethyl-2-imidazolidinone, sulfolane, and dimethyl sulfoxide; nitriles such as acetonitrile and propionitrile; esters such as ethyl acetate and butyl acetate; alcohols such as methanol and ethanol; inorganic acids such as sulfuric acid and hydrochloric acid; organic acids such as formic acid and acetic acid; and water. These solvents may be used singly, or in mixture of two or more thereof. Examples of the aldehyde include formaldehyde, acetaldehyde, and propionaldehyde.

The reaction temperature may be appropriately selected within the range of from −20° C. to the reflux temperature of the solvent to be used, and the reaction time may be appropriately selected within the range of from several minutes to 96 hours.

The method of producing the compound represented by Formula (4) preferably further includes a process of converting a compound which is represented by the following Formula (8) and in which $R^3$ represents a $C_1$-$C_6$ alkyl group, a $C_3$-$C_8$ cycloalkyl group, a $C_2$-$C_6$ alkenyl group, or a $C_2$-$C_6$ alkynyl group, to a compound represented by the following Formula (11) by hydrolysis utilizing a common technique or a method using a Pd catalyst or the like.

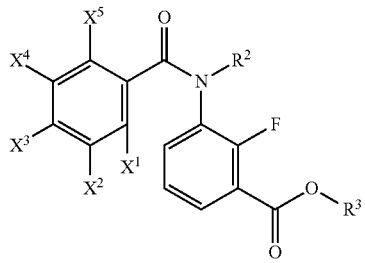

(8)

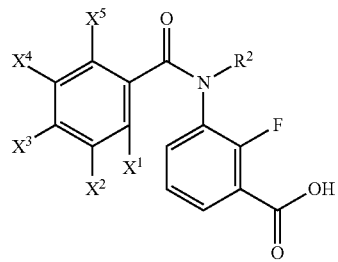

(11)

In Formula (11), $X^1$, $X^2$, $X^3$, $X^4$, $X^5$, and $R^2$ have the same definitions as $X^1$, $X^2$, $X^3$, $X^4$, $X^5$, and $R^2$ in Formula (8), respectively.

A compound represented by Formula (11) can be obtained from a compound which is represented by Formula (8) and in which $R^3$ represents a $C_1$-$C_6$ alkyl group, a $C_3$-$C_8$ cycloalkyl group, a $C_2$-$C_6$ alkenyl group, or a $C_2$-$C_6$ alkynyl group, by hydrolysis utilizing a common technique or a method using a Pd catalyst. The method involving hydrolysis is, for example, a method in which a compound represented by Formula (11) is obtained by basic hydrolysis using from equimolar to 5-fold molar excess of aqueous or alcoholic lithium hydroxide, sodium hydroxide, or potassium hydroxide in a single or mixed solvent of methanol, ethanol, tetrahydrofuran, or dioxane. The hydrolysis can be carried out even in a water-insoluble solvent such as toluene or xylene, by using a base such as aqueous sodium hydroxide, potassium hydroxide, or lithium hydroxide, and a phase transfer catalyst such as tetrabutylammonium bromide, benzyltriethylammonium chloride, or a crown ether, in combination. Acid hydrolysis can also be carried out using an inorganic acid such as hydrochloric acid or sulfuric acid, an organic acid such as acetic acid or trifluoroacetic acid, or a strongly acidic resin.

The reaction temperature may be appropriately selected within the range of from 20° C. to the reflux temperature of the solvent to be used. Further, the reaction time may be appropriately selected within the range of from several minutes to 96 hours.

As the method of using Pd, for example, a method described in Tetrahedron Letters, p. 4371 (1987) may be used.

The method of producing a compound represented by Formula (4) preferably further includes a process of converting a compound represented by the following Formula (11) to a compound represented by the following Formula (12).

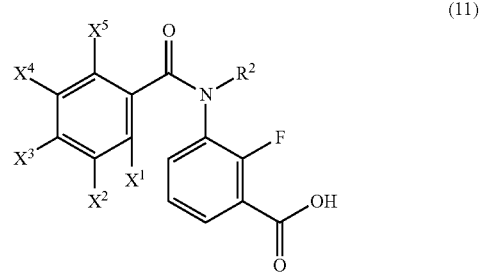

(11)

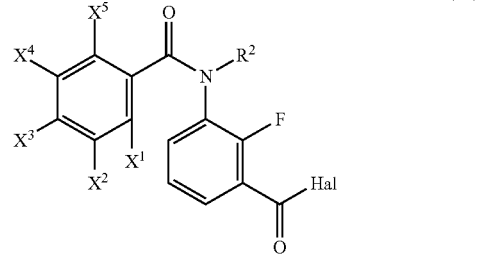

(12)

In Formula (12), $X^1$, $X^2$, $X^3$, $X^4$, $X^5$, and $R^2$ have the same definitions as $X^1$, $X^2$, $X^3$, $X^4$, $X^5$, and $R^2$ in Formula (11), respectively; and Hal represents a fluorine atom, a chlorine atom, or a bromine atom.

The compound represented by Formula (12) can be produced by treating a compound represented by Formula (11) with an equimolar or greater amount of halogenating agent.

Examples of the halogenating agent include thionyl chloride, thionyl bromide, oxalyl chloride, phosphorus oxychloride, oxalyl chloride, phosphorus trichloride, and phosphorus pentachloride.

This reaction may be carried out using a solvent, and the solvent may be any inert solvent. For example, one of, or two or more of, the following may be selected as the solvent: chain ethers or cyclic ethers such as diethyl ether, t-butyl ethyl ether, tetrahydrofuran, dioxane, and 1,2-dimethoxyethane; halogenated hydrocarbons such as methylene chloride, chloroform, carbon tetrachloride, dichloroethane, trichloroethane, dichloroethylene, chlorobenzene, and dichlorobenzene; aromatic hydrocarbons such as benzene, toluene, xylene, chlorobenzene, and dichlorobenzene; aliphatic hydrocarbons such as n-hexane, heptane, octane, and cyclohexane; esters such as ethyl acetate and butyl acetate; nitriles such as acetonitrile and propionitrile; and aprotic polar solvents such as N,N-dimethylformamide, N,N-dimethylacetamide, dimethyl sulfoxide, N-methylpyrrolidone, and 1,3-dimethyl-2-imidazolidinone.

The reaction can be carried out usually at −20° C. to 140° C., and the reaction time is usually appropriately selected within the range of from 0.1 hours to 96 hours.

Further, a compound represented by Formula (14) can be produced from, for example, a compound represented by the following Formula (15) in the following manner.

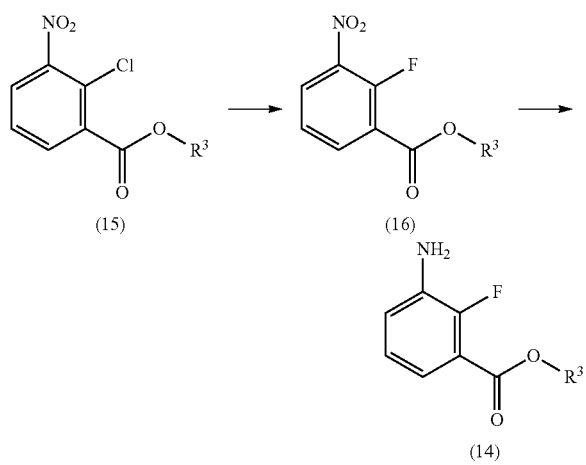

In Formula (15) and Formula (16), $R^3$ has the same definition as $R^3$ in Formula (14).

The compound represented by Formula (16) can be produced by allowing the compound represented by Formula (15) and a metal fluoride (such as at least one selected from the group consisting of lithium fluoride, sodium fluoride, potassium fluoride, cesium fluoride, and rubidium fluoride, or a mixture thereof) to react with each other in an appropriate solvent.

The metal fluoride is preferably sodium fluoride, potassium fluoride, or cesium fluoride. There are no particular limitations on the shape and production method of the metal fluoride. It is preferable to use a spray dried product or to perform heating treatment before use, and it is particularly preferable to perform heating treatment before use. The heating temperature is preferably from 50° C. to 250° C., and particularly preferably from 80° C. to 200° C.

The solvent to be used for the reaction may be any solvent that does not inhibit the progress of the reaction. Use of a polar organic solvent, which has high effect with respect to dissolution of metal fluorides, particularly increases the reaction rate, and thus is preferable. Specific examples thereof include: nitriles such as acetonitrile and propionitrile; ketones such as acetone, methyl isobutyl ketone, and methyl ethyl ketone; ethers such as tetrahydrofuran and dioxane; and aprotic polar solvents such as nitromethane, N,N-dimethylformamide, 1,3-dimethyl-2-imidazolidinone, dimethyl sulfoxide, sulfolane, N-methylpyrrolidone, and N,N-dimethylacetamide; N,N-dimethylformamide, dimethyl sulfoxide, and sulfolane are preferable.

The amount of the metal fluoride to be used is usually 1 mol or greater relative to the compound represented by Formula (15). In order to obtain the desired product with a sufficient yield, the amount is preferably from 1 to 10 mol, and particularly preferably from 1 to 5 mol, relative to the compound represented by Formula (15).

An additive may be used, and examples of the additive include: crown ethers such as 18-crown-6; phase transfer catalysts such as tetraphenylphosphonium salts; inorganic salts such as calcium fluoride and calcium chloride; metal oxides such as mercury oxide; and ion-exchange resins. These additives are not necessarily added to the reaction system, and may be used as a pretreatment agent for the fluorinating agent.

The compound represented by Formula (16) can be derivatized into a compound represented by Formula (14) by a reduction reaction.

Examples of the reduction reaction include a method of using a hydrogenation reaction, and a method of using a metal compound (such as stannous chloride (anhydride), iron powder, or zinc powder). In the former method, the reaction may be carried out in a solvent in the presence of a catalyst at normal pressure or increased pressure, under a hydrogen atmosphere. Examples of the catalyst include: palladium catalysts such as palladium/carbon; nickel catalysts such as Raney nickel; cobalt catalysts, ruthenium catalysts, rhodium catalysts, and platinum catalysts. The reaction may be carried out by, for example, using palladium/carbon in an amount, in terms of metal weight, of 1/10 times to 1/10,000 times the weight of the compound represented by Formula (16), at a hydrogen pressure of from 0.1 MPa to 10 MPa and a reaction temperature of usually from 0° C. to 100° C. for from several minutes to 96 hours while agitating. Examples of the solvent include: water; alcohols such as methanol and ethanol; chain ethers or cyclic ethers such as ether, dioxane, and tetrahydrofuran; esters such as ethyl acetate and butyl acetate; and aprotic polar solvents such as N,N-diemethylformamide, 1,3-dimethyl-2-imidazolidinone, dimethyl sulfoxide, sulfolane, N-methylpyrrolidone, and N,N-dimethylacetamide. These solvents are used singly, or in mixture.

The compound represented by Formula (14) can be efficiently produced thereby. In regard to the reaction of reducing the compound represented by Formula (16), a method of using stannous chloride (anhydride) as a metal compound and employing, for example, the conditions described in Organic Synthesis Coll., Vol. III, p. 453 may be used. However, the reaction conditions are not limited to the above conditions.

As described above, the compound represented by Formula (8) according to the invention is quite useful as a production intermediate in the method of producing an amide derivative represented by Formula (3).

The following Table 1 shows representative examples of compounds represented by Formula (8), but the compounds according to the invention are not limited thereto. In the Table, "n-" means normal, "i-" means iso-, "Me" means a methyl group, "Et" means an ethyl group, "n-Pr" means a normal propyl group, "n-Bu" means a normal butyl group, "n-Pn" means a normal pentyl group, "n-hex" means a normal hexyl group, "i-Pr" means an isopropyl group, "H" means a hydrogen atom, "F" means a fluorine atom, "Cl" means a chlorine atom, "CN" means a nitrile group, "Cyclo-Pr" means a cyclopropyl group, "Cyclo-hex" means a cyclohexyl group, "CH$_2$CH═CH$_2$" means an allyl group, "CH$_2$C≡CH" means a propargyl group, "CH$_2$OCH$_3$" means a methoxymethyl group, "CH$_2$Ph" means a benzyl group, "CH$_2$OCH$_2$Ph" means a benzyloxymethyl group, "C(CH$_3$)$_3$" means a t-butyl group, "CH$_2$CH$_2$Cl" means a 2-chloroethyl group, and "NO$_2$" means a nitro group.

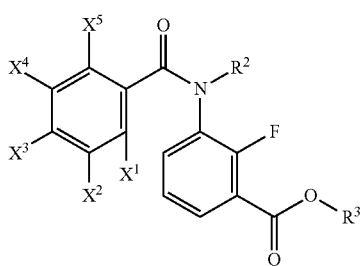

(8)

TABLE 1

| Compound No. | X¹ | X² | X³ | X⁴ | X⁵ | R² | R³ |
|---|---|---|---|---|---|---|---|
| 1-1 | H | H | H | H | H | H | Me |
| 1-2 | H | H | H | H | H | Me | Me |
| 1-3 | H | H | H | H | H | Me | H |
| 1-4 | H | H | H | H | H | H | Et |
| 1-5 | H | H | H | H | H | H | CH₂CH=CH₂ |
| 1-6 | H | H | H | H | H | Me | Cyclo-hex |
| 1-7 | H | H | H | H | H | H | n-Bu |
| 1-8 | H | H | H | H | H | Me | i-Pr |
| 1-9 | H | H | H | H | H | Me | n-Pr |
| 1-10 | H | H | H | H | H | Et | Me |
| 1-11 | H | H | H | H | H | Et | H |
| 1-12 | H | H | H | H | H | n-Pr | Me |
| 1-13 | H | H | H | H | H | n-Pr | H |
| 1-14 | H | H | H | H | H | i-Pr | CH₂OCH₃ |
| 1-15 | H | H | H | H | H | n-Pn | Me |
| 1-16 | H | H | H | H | H | n-Pn | CH₂C≡CH |
| 1-17 | H | H | H | H | H | n-hex | H |
| 1-18 | H | H | H | H | H | Cyclo-Pr | CH₂Ph |
| 1-19 | H | H | H | H | H | Cyclo-Pr | C(CH₃)₃ |
| 1-20 | H | H | F | H | H | H | Me |
| 1-21 | H | H | F | H | H | Me | Me |
| 1-22 | H | H | F | H | H | Me | H |
| 1-23 | H | H | F | H | H | H | CH₂CH₂Cl |
| 1-24 | H | H | F | H | H | H | CH₂OCH₃ |
| 1-25 | H | H | F | H | H | Me | Et |
| 1-26 | H | H | F | H | H | Et | Cyclo-hex |
| 1-27 | H | H | F | H | H | H | CH₂CH=CH₂ |
| 1-28 | H | H | F | H | H | H | n-Bu |
| 1-29 | H | H | F | H | H | Me | Et |
| 1-30 | H | H | F | H | H | Me | CH₂Ph |
| 1-31 | H | H | F | H | H | Et | Me |
| 1-32 | H | H | F | H | H | Et | H |
| 1-33 | H | H | F | H | H | i-Pr | CH₂C≡CH |
| 1-34 | H | H | F | H | H | i-Pr | CH₂OCH₃ |
| 1-35 | H | H | F | H | H | n-Bu | H |
| 1-36 | H | H | F | H | H | Cyclo-Pr | CH₂C≡CH |
| 1-37 | H | H | F | H | H | Cyclo-Pr | CH₂OCH₂Ph |
| 1-38 | H | H | F | H | H | Cyclo-Pr | Et |
| 1-39 | F | H | H | H | H | H | Me |
| 1-40 | F | H | H | H | H | Me | Me |
| 1-41 | F | H | H | H | H | Me | H |
| 1-42 | F | H | H | H | H | H | CH₂CH₂Cl |
| 1-43 | F | H | H | H | H | H | CH₂OCH₃ |
| 1-44 | F | H | H | H | H | Me | Et |
| 1-45 | F | H | H | H | H | Et | Cyclo-hex |
| 1-46 | F | H | H | H | H | H | CH₂CH=CH₂ |
| 1-47 | F | H | H | H | H | H | n-Bu |
| 1-48 | F | H | H | H | H | Me | Et |
| 1-49 | F | H | H | H | H | Et | Me |
| 1-50 | F | H | H | H | H | Et | H |
| 1-51 | F | H | H | H | H | n-Pr | H |
| 1-52 | F | H | H | H | H | i-Pr | Me |
| 1-53 | F | H | H | H | H | i-Pr | H |
| 1-54 | F | H | H | H | H | i-Pr | CH₂Ph |
| 1-55 | F | H | H | H | H | n-Bu | Me |
| 1-56 | F | H | H | H | H | n-Bu | H |
| 1-57 | F | H | H | H | H | n-hex | CH₂OCH₃ |
| 1-58 | F | H | H | H | H | n-hex | H |
| 1-59 | F | H | H | H | H | Cyclo-Pr | CH₂OCH₂Ph |
| 1-60 | F | H | H | H | H | Cyclo-Pr | Me |
| 1-61 | F | H | H | H | H | Cyclo-Pr | Et |
| 1-62 | F | H | H | H | H | Cyclo-Pr | n-Pr |
| 1-63 | H | F | H | H | H | H | Me |
| 1-64 | H | F | H | H | H | Me | Me |
| 1-65 | H | F | H | H | H | Me | H |
| 1-66 | H | F | H | H | H | H | CH₂CH=CH₂ |
| 1-67 | H | F | H | H | H | H | Cyclo-hex |
| 1-68 | H | F | H | H | H | Et | Et |
| 1-69 | H | F | H | H | H | H | CH₂OCH₃ |
| 1-70 | H | F | H | H | H | H | CH₂OCH₂Ph |
| 1-71 | H | F | H | H | H | Me | Et |
| 1-72 | H | F | H | H | H | Et | Me |
| 1-73 | H | F | H | H | H | Et | H |
| 1-74 | H | F | H | H | H | n-Pr | H |
| 1-75 | H | F | H | H | H | i-Pr | H |
| 1-76 | H | F | H | H | H | i-Pr | CH₂Ph |
| 1-77 | H | F | H | H | H | n-Bu | Me |
| 1-78 | H | F | H | H | H | n-Bu | H |
| 1-79 | H | F | H | H | H | n-Pn | H |
| 1-80 | H | F | H | H | H | n-hex | CH₂Ph |
| 1-81 | H | F | H | H | H | n-hex | H |
| 1-82 | H | F | H | H | H | Cyclo-Pr | CH₂OCH₃ |
| 1-83 | H | F | H | H | H | Cyclo-Pr | Me |
| 1-84 | F | H | H | H | F | H | Me |
| 1-85 | F | H | H | H | F | Me | H |
| 1-86 | F | H | H | H | F | H | CH₂OCH₃ |
| 1-87 | F | H | H | H | F | H | Cyclo-hex |
| 1-88 | F | H | H | H | F | Me | CH₂Ph |
| 1-89 | F | H | H | H | F | Et | Et |
| 1-90 | F | H | H | H | F | H | CH₂CH=CH₂ |
| 1-91 | F | H | H | H | F | H | CH₂OCH₂Ph |
| 1-92 | F | H | H | H | F | Me | Et |
| 1-93 | F | H | H | H | F | Me | CH₂C≡CH |
| 1-94 | F | H | H | H | F | Et | Me |
| 1-95 | F | H | H | H | F | Et | H |
| 1-96 | F | H | H | H | F | i-Pr | Me |
| 1-97 | F | H | H | H | F | i-Pr | H |
| 1-98 | F | H | H | H | F | n-Pn | H |
| 1-99 | F | H | H | H | F | n-hex | H |
| 1-100 | F | H | H | H | F | Cyclo-Pr | CH₂OCH₂Ph |
| 1-101 | F | H | H | H | F | Cyclo-Pr | Me |
| 1-102 | H | H | CN | H | H | H | Me |
| 1-103 | H | H | CN | H | H | Me | Me |
| 1-104 | H | H | CN | H | H | Me | H |
| 1-105 | H | H | CN | H | H | H | CH₂OCH₃ |
| 1-106 | H | H | CN | H | H | H | Cyclo-hex |
| 1-107 | H | H | CN | H | H | Me | CH₂Ph |
| 1-108 | H | H | CN | H | H | Et | Et |
| 1-109 | H | H | CN | H | H | H | CH₂CH=CH₂ |
| 1-110 | H | H | CN | H | H | H | CH₂OCH₂Ph |
| 1-111 | H | H | CN | H | H | Me | Et |
| 1-112 | H | H | CN | H | H | Et | Me |
| 1-113 | H | H | CN | H | H | Et | H |
| 1-114 | H | H | CN | H | H | n-Pr | H |
| 1-115 | H | H | CN | H | H | i-Pr | H |
| 1-116 | H | H | CN | H | H | n-Bu | H |
| 1-117 | H | H | CN | H | H | n-hex | Me |
| 1-118 | H | H | CN | H | H | Cyclo-Pr | CH₂OCH₂Ph |
| 1-119 | H | H | CN | H | H | Cyclo-Pr | Et |
| 1-120 | H | CN | H | H | H | H | Me |
| 1-121 | H | CN | H | H | H | Me | Me |
| 1-122 | H | CN | H | H | H | Me | H |
| 1-123 | H | CN | H | H | H | H | CH₂CH=CH₂ |
| 1-124 | H | CN | H | H | H | H | CH₂OCH₂Ph |
| 1-125 | H | CN | H | H | H | H | CH₂Ph |
| 1-126 | H | CN | H | H | H | H | CH₂OCH₃ |
| 1-127 | H | CN | H | H | H | Me | Et |
| 1-128 | H | CN | H | H | H | Et | Me |
| 1-129 | H | CN | H | H | H | Et | H |
| 1-130 | H | CN | H | H | H | n-Pr | H |
| 1-131 | H | CN | H | H | H | i-Pr | H |
| 1-132 | H | CN | H | H | H | n-Bu | Me |
| 1-133 | H | CN | H | H | H | n-Bu | H |
| 1-134 | H | CN | H | H | H | n-hex | H |
| 1-135 | H | CN | H | H | H | Cyclo-Pr | CH₂OCH₂Ph |
| 1-136 | H | CN | H | H | H | Cyclo-Pr | Me |
| 1-137 | H | H | F | H | Cl | H | Me |
| 1-138 | H | H | F | H | Cl | Me | Me |

TABLE 1-continued

| Compound No. | X¹ | X² | X³ | X⁴ | X⁵ | R² | R³ |
|---|---|---|---|---|---|---|---|
| 1-139 | H | H | F | H | Cl | Me | H |
| 1-140 | H | H | F | H | Cl | H | CH₂CH=CH₂ |
| 1-141 | H | H | F | H | Cl | H | CH₂OCH₂Ph |
| 1-142 | H | H | F | H | Cl | Me | CH₂C≡CH |
| 1-143 | H | H | F | H | Cl | Et | Et |
| 1-144 | H | H | F | H | Cl | H | CH₂OCH₃ |
| 1-145 | H | H | F | H | Cl | H | Cyclo-hex |
| 1-146 | H | H | F | H | Cl | Et | Me |
| 1-147 | H | H | F | H | Cl | n-Pr | H |
| 1-148 | H | H | F | H | Cl | i-Pr | Me |
| 1-149 | H | H | F | H | Cl | n-Bu | H |
| 1-150 | H | H | F | H | Cl | n-hex | H |
| 1-151 | H | H | F | H | Cl | Cyclo-Pr | CH₂OCH₂Ph |
| 1-152 | H | H | F | H | Cl | Cyclo-Pr | Me |
| 1-153 | H | H | F | H | Cl | Cyclo-Pr | Et |
| 1-154 | H | H | NO₂ | H | H | H | Me |
| 1-155 | H | H | NO₂ | H | H | Me | Me |
| 1-156 | H | H | NO₂ | H | H | Me | H |
| 1-157 | H | H | NO₂ | H | H | Et | CH₂OCH₃ |
| 1-158 | H | H | H | NO₂ | H | H | Me |
| 1-159 | H | H | H | NO₂ | H | Me | Me |
| 1-160 | H | H | H | NO₂ | H | Me | H |

The following Table 2 shows representative examples of compounds represented by Formula (12), which are useful production intermediates in the method of producing an amide compound according to the invention. However, the invention is not limited thereto. In the Table, "n-" means normal, "i-" means iso-, "Me" means a methyl group, "Et" means an ethyl group, "n-Pr" means a normal propyl group, "n-Bu" means a normal butyl group, "n-Pn" means a normal pentyl group, "n-hex" means a normal hexyl group, "i-Pr" means an isopropyl group, "H" means a hydrogen atom, "F" means a fluorine atom, "Cl" means a chlorine atom, "Br" represents a bromine atom, "CN" means a nitrile group, "NO₂" means a nitro group, and "Cyclo-Pr" means a cyclopropyl group.

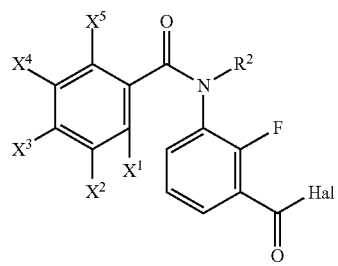

(12)

TABLE 2

| Compound No. | X¹ | X² | X³ | X⁴ | X⁵ | R² | Hal |
|---|---|---|---|---|---|---|---|
| 2-1 | H | H | H | H | H | H | F |
| 2-2 | H | H | H | H | H | H | Cl |
| 2-3 | H | H | H | H | H | H | Br |
| 2-4 | H | H | H | H | H | Me | F |
| 2-5 | H | H | H | H | H | Me | Cl |
| 2-6 | H | H | H | H | H | Me | Br |
| 2-7 | H | H | H | H | H | Et | Cl |
| 2-8 | H | H | H | H | H | n-Pr | Br |
| 2-9 | H | H | H | H | H | i-Pr | Cl |
| 2-10 | H | H | H | H | H | n-Bu | Cl |
| 2-11 | H | H | H | H | H | n-Pn | Cl |
| 2-12 | H | H | F | H | H | H | Br |
| 2-13 | H | H | F | H | H | H | F |
| 2-14 | H | H | F | H | H | H | Cl |
| 2-15 | H | H | F | H | H | Me | Cl |
| 2-16 | H | H | F | H | H | Me | Br |
| 2-17 | H | H | F | H | H | Et | Cl |
| 2-18 | H | H | F | H | H | Et | Br |
| 2-19 | H | H | F | H | H | n-Pr | Cl |
| 2-20 | H | H | F | H | H | i-Pr | Br |
| 2-21 | H | H | F | H | H | n-Bu | Cl |
| 2-22 | H | H | F | H | H | n-Pn | Cl |
| 2-23 | H | H | F | H | H | n-hex | Cl |
| 2-24 | H | H | F | H | H | Cyclo-Pr | Cl |
| 2-25 | H | H | H | F | H | H | Br |
| 2-26 | H | H | H | F | H | H | F |
| 2-27 | H | H | H | F | H | H | Cl |
| 2-28 | H | H | H | F | H | Me | Cl |
| 2-29 | H | H | H | F | H | Me | Br |
| 2-30 | H | H | H | F | H | Et | Cl |
| 2-31 | H | H | H | F | H | Et | Br |
| 2-32 | H | H | H | F | H | n-Pr | Cl |
| 2-33 | H | H | H | F | H | i-Pr | Cl |
| 2-34 | H | H | H | F | H | i-Pr | Br |
| 2-35 | H | H | H | F | H | n-Bu | Cl |
| 2-36 | H | H | H | F | H | n-hex | Cl |
| 2-37 | F | H | H | H | F | H | Br |
| 2-38 | F | H | H | H | F | H | F |
| 2-39 | F | H | H | H | F | H | Cl |
| 2-40 | F | H | H | H | F | Me | Cl |
| 2-41 | F | H | H | H | F | Me | Br |
| 2-42 | F | H | H | H | F | Et | Cl |
| 2-43 | F | H | H | H | F | Et | Br |
| 2-44 | F | H | H | H | F | i-Pr | Cl |
| 2-45 | F | H | H | H | F | i-Pr | Br |
| 2-46 | F | H | H | H | F | n-Bu | Cl |
| 2-47 | F | H | H | H | F | n-Pn | Cl |
| 2-48 | F | H | H | H | F | n-hex | Cl |
| 2-49 | F | H | H | H | H | H | Br |
| 2-50 | F | H | H | H | H | H | F |
| 2-51 | F | H | H | H | H | H | Cl |
| 2-52 | F | H | H | H | H | Me | Cl |
| 2-53 | F | H | H | H | H | Me | Br |
| 2-54 | F | H | H | H | H | Et | Cl |
| 2-55 | F | H | H | H | H | Et | Br |
| 2-56 | F | H | H | H | H | n-Pr | Cl |
| 2-57 | F | H | H | H | H | i-Pr | Cl |
| 2-58 | F | H | H | H | H | i-Pr | Br |
| 2-59 | F | H | H | H | H | n-Bu | Cl |
| 2-60 | F | H | H | H | H | n-Pn | Cl |
| 2-61 | F | H | H | H | H | n-hex | Cl |
| 2-62 | F | H | H | H | H | Cyclo-Pr | Cl |
| 2-63 | H | H | F | H | Cl | H | Br |
| 2-64 | H | H | F | H | Cl | H | F |
| 2-65 | H | H | F | H | Cl | H | Cl |
| 2-66 | H | H | F | H | Cl | Me | Cl |
| 2-67 | H | H | F | H | Cl | Me | Br |
| 2-68 | H | H | F | H | Cl | Et | Cl |
| 2-69 | H | H | F | H | Cl | Et | Br |
| 2-70 | H | H | F | H | Cl | n-Pr | Cl |
| 2-71 | H | H | F | H | Cl | i-Pr | Cl |
| 2-72 | H | H | F | H | Cl | i-Pr | Br |
| 2-73 | H | H | F | H | Cl | n-Bu | Cl |
| 2-74 | H | H | F | H | Cl | n-Pn | Cl |
| 2-75 | H | H | F | H | Cl | n-hex | Cl |
| 2-76 | H | H | F | H | Cl | Cyclo-Pr | Cl |
| 2-77 | H | H | CN | H | H | H | Br |
| 2-78 | H | H | CN | H | H | H | F |
| 2-79 | H | H | CN | H | H | H | Cl |
| 2-80 | H | H | CN | H | H | Me | Cl |
| 2-81 | H | H | CN | H | H | Me | Br |
| 2-82 | H | H | CN | H | H | Et | Cl |
| 2-83 | H | H | CN | H | H | Et | Br |
| 2-84 | H | H | CN | H | H | n-Pr | Cl |
| 2-85 | H | H | CN | H | H | i-Pr | Cl |
| 2-86 | H | H | CN | H | H | i-Pr | Br |
| 2-87 | H | H | CN | H | H | n-Bu | Cl |
| 2-88 | H | H | CN | H | H | n-Pn | Cl |
| 2-89 | H | H | CN | H | H | n-hex | Cl |
| 2-90 | H | H | CN | H | H | Cyclo-Pr | Cl |
| 2-91 | H | H | H | CN | H | H | Br |
| 2-92 | H | H | H | CN | H | H | F |

TABLE 2-continued

| Compound No. | $X^1$ | $X^2$ | $X^3$ | $X^4$ | $X^5$ | $R^2$ | Hal |
|---|---|---|---|---|---|---|---|
| 2-93 | H | H | H | CN | H | H | Cl |
| 2-94 | H | H | H | CN | H | Me | Cl |
| 2-95 | H | H | H | CN | H | Me | Br |
| 2-96 | H | H | H | CN | H | Et | Cl |
| 2-97 | H | H | H | CN | H | Et | Br |
| 2-98 | H | H | H | CN | H | n-Pr | Cl |
| 2-99 | H | H | H | CN | H | i-Pr | Cl |
| 2-100 | H | H | H | H | CN | Me | Br |
| 2-101 | H | H | H | H | CN | Et | Cl |
| 2-102 | H | H | H | H | CN | n-Pr | Cl |
| 2-103 | H | H | H | H | CN | n-Bu | Cl |
| 2-104 | H | H | $NO_2$ | H | H | H | Br |
| 2-105 | H | H | $NO_2$ | H | H | H | F |
| 2-106 | H | H | $NO_2$ | H | H | H | Cl |
| 2-107 | H | H | $NO_2$ | H | H | Me | Cl |
| 2-108 | H | H | $NO_2$ | H | H | Me | Br |
| 2-109 | H | H | $NO_2$ | H | H | Et | Cl |
| 2-110 | H | H | H | $NO_2$ | H | Et | Br |
| 2-111 | H | H | H | $NO_2$ | H | H | Br |
| 2-112 | H | H | H | $NO_2$ | H | H | Cl |
| 2-113 | H | H | H | $NO_2$ | H | Me | Br |
| 2-114 | H | H | H | $NO_2$ | H | Me | Cl |
| 2-115 | H | H | H | H | $NO_2$ | Me | Cl |
| 2-116 | H | H | H | H | $NO_2$ | Et | Cl |

The following Table 3 shows representative examples of amide derivatives represented by Formula (3) obtained by the method of producing an amide compound according to the invention. However, the invention is not limited thereto. In the Table, "n-" means normal, "i-" means iso-, "s-" represents secondary, "Me" means a methyl group, "Et" means an ethyl group, "n-Pr" means a normal propyl group, "$CF_3$" represents a trifluoromethyl group, "H" means a hydrogen atom, "F" means a fluorine atom, "Cl" means a chlorine atom, "Br" represents a bromine atom, "I" represents an iodine atom, "CN" means a nitrile group, "$NO_2$" means a nitro group, "$OCF_3$" represents a trifluoromethoxy group, "CH" represents a methine group, and "N" represents a nitrogen atom.

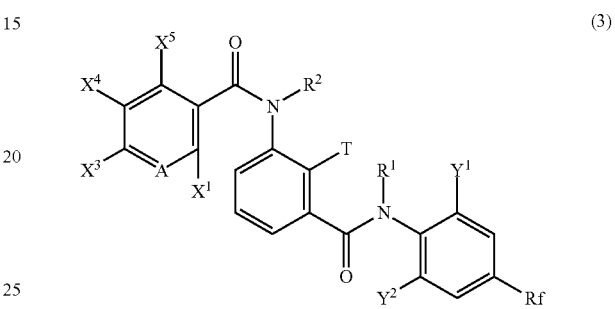

(3)

TABLE 3

| Compound No. | $X^1$ | $X^3$ | $X^4$ | $X^5$ | A | T | $R^1$ | $R^2$ | $Y^1$ | $Y^2$ | Rf |
|---|---|---|---|---|---|---|---|---|---|---|---|
| 3-1 | H | H | H | H | CH | F | H | Me | Br | $CF_3$ | perfluoro-i-propyl |
| 3-2 | H | H | H | H | CH | F | H | Me | Br | Br | perfluoro-i-propyl |
| 3-3 | H | H | H | H | CH | F | H | Me | I | I | perfluoro-i-propyl |
| 3-4 | H | H | H | H | CH | F | H | Me | I | Br | perfluoro-i-propyl |
| 3-5 | H | H | H | H | CH | F | H | Me | Br | Br | perfluoro-s-butyl |
| 3-6 | H | H | H | H | CH | F | H | Me | Br | $CF_3$ | perfluoro-s-butyl |
| 3-7 | H | H | H | H | CH | F | H | Me | I | $CF_3$ | perfluoro-i-propyl |
| 3-8 | H | H | H | H | CH | F | H | Me | I | I | perfluoro-s-butyl |
| 3-9 | H | H | H | H | CH | F | H | Me | I | $CF_3$ | perfluoro-s-butyl |
| 3-10 | H | H | H | H | CH | F | H | Me | Cl | $CF_3$ | perfluoro-i-propyl |
| 3-11 | H | H | H | H | CH | F | H | H | I | $CF_3$ | perfluoro-i-propyl |
| 3-12 | H | H | H | H | CH | F | H | H | I | I | perfluoro-s-butyl |
| 3-13 | H | H | H | H | CH | F | H | H | Br | Br | perfluoro-s-butyl |
| 3-14 | H | H | H | H | CH | F | H | H | Br | Br | perfluoro-i-propyl |
| 3-15 | H | H | H | H | CH | F | H | H | $CF_3$ | $CF_3$ | perfluoro-i-propyl |
| 3-16 | H | H | H | H | CH | F | H | H | I | I | perfluoro-i-propyl |
| 3-17 | H | H | H | H | CH | F | H | H | Br | $CF_3$ | perfluoro-i-propyl |
| 3-18 | H | H | H | H | CH | H | H | Me | Br | $CF_3$ | perfluoro-i-propyl |
| 3-19 | H | H | H | H | CH | H | H | Me | I | $CF_3$ | perfluoro-i-propyl |
| 3-20 | H | H | H | H | CH | F | H | Me | Br | $OCF_3$ | perfluoro-i-propyl |
| 3-21 | H | F | H | H | CH | F | H | Me | Br | $CF_3$ | perfluoro-i-propyl |
| 3-22 | H | F | H | H | CH | F | H | Me | Br | $CF_3$ | perfluoro-s-butyl |
| 3-23 | H | F | H | H | CH | F | H | Me | I | $CF_3$ | perfluoro-i-propyl |
| 3-24 | H | F | H | H | CH | F | H | Me | I | $CF_3$ | perfluoro-s-butyl |
| 3-25 | H | F | H | H | CH | F | H | Me | Br | Br | perfluoro-s-butyl |
| 3-26 | H | F | H | H | CH | F | H | Me | Br | $OCF_3$ | perfluoro-i-propyl |
| 3-27 | H | F | H | H | CH | F | H | Me | I | I | perfluoro-i-propyl |
| 3-28 | H | F | H | H | CH | F | H | H | Br | Br | perfluoro-i-propyl |
| 3-29 | H | F | H | H | CH | F | H | H | I | I | perfluoro-s-butyl |
| 3-30 | H | F | H | H | CH | F | H | H | I | $CF_3$ | perfluoro-i-propyl |
| 3-31 | H | F | H | H | CH | F | H | H | Br | $CF_3$ | perfluoro-i-propyl |
| 3-32 | H | F | H | H | CH | F | H | H | I | I | perfluoro-i-propyl |
| 3-33 | H | F | H | H | CH | H | H | Me | I | $CF_3$ | perfluoro-i-propyl |
| 3-34 | H | H | F | H | CH | F | H | Me | I | $CF_3$ | perfluoro-i-propyl |
| 3-35 | H | H | F | H | CH | F | H | Me | Br | $CF_3$ | perfluoro-i-propyl |
| 3-36 | H | H | F | H | CH | F | H | Me | I | I | perfluoro-s-butyl |
| 3-37 | H | H | F | H | CH | F | H | Me | Br | Br | perfluoro-s-butyl |
| 3-38 | H | H | F | H | CH | F | H | Me | I | I | perfluoro-i-propyl |
| 3-39 | H | H | F | H | CH | F | H | Me | Br | Br | perfluoro-i-propyl |
| 3-40 | H | H | F | H | CH | F | H | Me | I | $CF_3$ | perfluoro-s-butyl |
| 3-41 | H | H | F | H | CH | F | H | H | Br | Br | perfluoro-i-propyl |
| 3-42 | H | H | F | H | CH | F | H | H | Br | Br | perfluoro-s-butyl |
| 3-43 | H | H | F | H | CH | H | H | H | Br | Br | perfluoro-s-butyl |

TABLE 3-continued

| Compound No. | X¹ | X³ | X⁴ | X⁵ | A | T | R¹ | R² | Y¹ | Y² | Rf |
|---|---|---|---|---|---|---|---|---|---|---|---|
| 3-44 | H | H | F | H | CH | F | H | H | I | I | perfluoro-s-butyl |
| 3-45 | H | H | F | H | CH | F | H | H | Br | CF₃ | perfluoro-i-propyl |
| 3-46 | H | H | F | H | CH | F | H | H | I | CF₃ | perfluoro-i-propyl |
| 3-47 | H | H | F | H | CH | H | H | H | Br | Br | perfluoro-s-butyl |
| 3-48 | H | H | F | H | CH | H | H | Me | Br | CF₃ | perfluoro-s-butyl |
| 3-49 | F | H | H | H | CH | F | H | Me | I | CF₃ | perfluoro-i-propyl |
| 3-50 | F | H | H | H | CH | F | H | Me | Br | CF₃ | perfluoro-i-propyl |
| 3-51 | F | H | H | H | CH | F | H | Me | I | I | perfluoro-s-butyl |
| 3-52 | F | H | H | H | CH | F | H | Me | Br | Br | perfluoro-s-butyl |
| 3-53 | F | H | H | H | CH | F | H | Me | Br | Br | perfluoro-i-propyl |
| 3-54 | F | H | H | H | CH | F | H | Me | I | CF₃ | perfluoro-s-butyl |
| 3-55 | F | H | H | H | CH | F | H | H | Br | Br | perfluoro-s-butyl |
| 3-56 | F | H | H | H | CH | H | H | H | Br | Br | perfluoro-s-butyl |
| 3-57 | F | H | H | H | CH | H | H | Me | Br | Br | perfluoro-s-butyl |
| 3-58 | F | H | H | F | CH | F | H | Me | I | CF₃ | perfluoro-i-propyl |
| 3-59 | F | H | H | F | CH | F | H | Me | Br | CF₃ | perfluoro-i-propyl |
| 3-60 | F | H | H | F | CH | F | H | Me | I | I | perfluoro-s-butyl |
| 3-61 | F | H | H | F | CH | F | H | Me | I | I | perfluoro-i-propyl |
| 3-62 | F | H | H | F | CH | F | H | Me | Br | Br | perfluoro-i-propyl |
| 3-63 | F | H | H | F | CH | F | H | H | I | I | perfluoro-s-butyl |
| 3-64 | F | H | H | F | CH | F | H | H | Br | CF₃ | perfluoro-i-propyl |
| 3-65 | F | H | H | F | CH | H | H | Me | I | CF₃ | perfluoro-i-propyl |
| 3-66 | F | H | H | F | CH | H | H | H | I | CF₃ | perfluoro-i-propyl |
| 3-67 | H | CN | H | H | CH | F | H | Me | Br | CF₃ | perfluoro-i-propyl |
| 3-68 | H | CN | H | H | CH | F | H | Me | Br | Br | perfluoro-i-propyl |
| 3-69 | H | CN | H | H | CH | F | H | Me | I | I | perfluoro-i-propyl |
| 3-70 | H | CN | H | H | CH | F | H | Me | Br | Br | perfluoro-s-butyl |
| 3-71 | H | CN | H | H | CH | F | H | Me | Br | CF₃ | perfluoro-s-butyl |
| 3-72 | H | CN | H | H | CH | F | H | Me | I | CF₃ | perfluoro-i-propyl |
| 3-73 | H | CN | H | H | CH | F | H | Me | I | I | perfluoro-s-butyl |
| 3-74 | H | CN | H | H | CH | F | H | Me | I | CF₃ | perfluoro-s-butyl |
| 3-75 | H | CN | H | H | CH | F | H | H | Br | CF₃ | perfluoro-i-propyl |
| 3-76 | H | CN | H | H | CH | F | H | H | Br | Br | perfluoro-i-propyl |
| 3-77 | H | CN | H | H | CH | F | H | H | I | I | perfluoro-s-butyl |
| 3-78 | H | CN | H | H | CH | F | H | H | Br | Br | perfluoro-s-butyl |
| 3-79 | H | CN | H | H | CH | F | H | H | Br | CF₃ | perfluoro-i-propyl |
| 3-80 | H | CN | H | H | CH | H | H | Me | Br | CF₃ | perfluoro-i-propyl |
| 3-81 | H | H | CN | H | CH | F | H | Me | Br | CF₃ | perfluoro-i-propyl |
| 3-82 | H | H | CN | H | CH | F | H | Me | Br | Br | perfluoro-i-propyl |
| 3-83 | H | H | CN | H | CH | F | H | Me | Br | Br | perfluoro-s-butyl |
| 3-84 | H | H | CN | H | CH | F | H | Me | Br | CF₃ | perfluoro-s-butyl |
| 3-85 | H | H | CN | H | CH | F | H | Me | I | I | perfluoro-s-butyl |
| 3-86 | H | H | CN | H | CH | F | H | Me | I | CF₃ | perfluoro-i-propyl |
| 3-87 | H | H | CN | H | CH | F | H | Me | I | I | perfluoro-i-propyl |
| 3-88 | H | H | CN | H | CH | F | H | Me | I | CF₃ | perfluoro-s-butyl |
| 3-89 | H | H | CN | H | CH | F | H | H | Br | Br | perfluoro-i-propyl |
| 3-90 | H | H | CN | H | CH | F | H | H | I | I | perfluoro-i-propyl |
| 3-91 | H | H | CN | H | CH | F | H | H | Br | CF₃ | perfluoro-i-propyl |
| 3-92 | H | H | CN | H | CH | F | H | H | Br | Br | perfluoro-s-butyl |
| 3-93 | H | H | CN | H | CH | H | H | Me | Br | CF₃ | perfluoro-s-butyl |
| 3-94 | F | CN | H | H | CH | H | H | Me | Br | CF₃ | perfluoro-i-propyl |
| 3-95 | Cl | CN | H | H | CH | H | H | Me | Br | CF₃ | perfluoro-i-propyl |
| 3-96 | H | H | H | H | CH | F | H | Et | Br | CF₃ | perfluoro-i-propyl |
| 3-97 | H | H | H | H | CH | F | H | Et | Br | CF₃ | perfluoro-s-butyl |
| 3-98 | H | H | H | H | CH | F | H | Et | I | CF₃ | perfluoro-i-propyl |
| 3-99 | H | H | H | H | CH | F | H | Et | I | CF₃ | perfluoro-s-butyl |
| 3-100 | H | H | H | H | CH | F | H | n-Pr | Br | CF₃ | perfluoro-i-propyl |
| 3-101 | H | H | H | H | CH | F | H | i-Pr | Br | CF₃ | perfluoro-s-butyl |
| 3-102 | H | H | H | H | CH | F | H | n-Pr | I | CF₃ | perfluoro-i-propyl |
| 3-103 | H | H | H | H | CH | F | H | n-Pr | I | CF₃ | perfluoro-s-butyl |
| 3-104 | H | F | H | Cl | CH | F | H | H | I | CF₃ | perfluoro-i-propyl |
| 3-105 | H | F | H | Cl | CH | H | H | H | I | CF₃ | perfluoro-i-propyl |
| 3-106 | H | F | H | Cl | CH | H | H | Me | I | CF₃ | perfluoro-i-propyl |
| 3-107 | H | F | H | Cl | CH | H | H | H | Br | CF₃ | perfluoro-i-propyl |
| 3-108 | H | F | H | Cl | CH | H | H | H | I | I | perfluoro-i-propyl |
| 3-109 | H | F | H | Cl | CH | H | H | H | Br | Br | perfluoro-i-propyl |
| 3-110 | H | NO₂ | H | H | CH | F | H | Me | Br | CF₃ | perfluoro-i-propyl |
| 3-111 | H | NO₂ | H | H | CH | H | H | Me | Br | CF₃ | perfluoro-s-butyl |
| 3-112 | H | NO₂ | H | H | CH | F | H | Me | I | CF₃ | perfluoro-i-propyl |
| 3-113 | H | NO₂ | H | H | CH | F | H | Me | I | CF₃ | perfluoro-s-butyl |
| 3-114 | H | H | NO₂ | H | CH | F | H | Me | Br | CF₃ | perfluoro-i-propyl |
| 3-115 | H | H | NO₂ | H | CH | F | H | Me | Br | Br | perfluoro-s-butyl |
| 3-116 | H | H | NO₂ | H | CH | F | H | Me | I | CF₃ | perfluoro-i-propyl |
| 3-117 | H | H | NO₂ | H | CH | F | H | Me | I | CF₃ | perfluoro-s-butyl |
| 3-118 | Cl | H | H | H | N | H | H | H | Br | CF₃ | perfluoro-i-propyl |
| 3-119 | Cl | H | H | H | N | H | H | H | I | CF₃ | perfluoro-i-propyl |
| 3-120 | Cl | H | H | H | N | F | H | H | I | CF₃ | perfluoro-i-propyl |
| 3-121 | Cl | H | H | H | N | H | H | H | Br | CF₃ | perfluoro-s-butyl |

TABLE 3-continued

| Compound No. | $X^1$ | $X^3$ | $X^4$ | $X^5$ | A | T | $R^1$ | $R^2$ | $Y^1$ | $Y^2$ | Rf |
|---|---|---|---|---|---|---|---|---|---|---|---|
| 3-122 | Cl | H | H | H | N | H | H | H | I | $CF_3$ | perfluoro-s-butyl |
| 3-123 | Cl | H | H | H | N | H | H | H | I | I | perfluoro-s-butyl |
| 3-124 | H | Cl | H | H | N | H | H | H | I | I | perfluoro-i-propyl |
| 3-125 | H | Cl | H | H | N | H | H | H | Br | $CF_3$ | perfluoro-i-propyl |
| 3-126 | I | H | H | H | N | H | H | H | Br | $CF_3$ | perfluoro-i-propyl |
| 3-127 | Br | H | H | H | N | H | H | H | Br | $CF_3$ | perfluoro-i-propyl |
| 3-128 | Br | H | H | H | N | H | H | H | Br | $OCF_3$ | perfluoro-i-propyl |
| 3-129 | Br | H | H | H | N | H | H | H | I | $CF_3$ | perfluoro-i-propyl |
| 3-130 | F | H | H | H | N | H | H | H | Br | $OCF_3$ | perfluoro-i-propyl |

The pest control agent including an amide derivative as an active ingredient represented by Formula (3) and produced using the compound of the invention can effectively control, at low concentrations, any of the pests including insects such as various agricultural insect pests that damage agricultural/horticultural products, trees, and the like, hygiene insect pests that adversely affects the living environment of humans such as houses, stored grain insect pests that damage animal drugs for pets or grains or the like stored in a warehouse, wood-eating insect pests damaging wood such as of buildings or the like, and mites, crustaceans, molluscs, and nematodes which occur and cause damage in situations similar to those described above.

Specific examples of the insects, the mites, the crustaceans, the molluscs, and the nematodes that can be controlled using an amide derivative represented by Formula (3) and produced by using the compound according to the invention include the following: lepidopteran insects such as *Adoxophyes honmai, Adoxophyes orana faciata, Archips breviplicanus, Grapholita inopinata, Archips fuscocupreanus, Grapholita molesta, Choristoneura magnanima, Leguminivora glycinivorella, Olethreutes mori, Caloptilia zachrysa, Argyresthia conjugella, Spulerrina astaurota, Matsumuraeses phaseoli, Pandemis heparana, Bucculatrix pyrivorella, Lyonetia clerkella, Carposina niponensis, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Chilo suppressalis, Cnaphalocrocis medinalis, Ephestia elutella, Conogethes punctiferalis, Diaphania indica, Etiella zinckenella, Glyphodes pyloalis, Scirpophaga incertulas, Hellula undalis, Ostrinia furnacalis, Ostrinia scapulalis, Parapediasia teterrella, Parnara guttata, Pieris brassicae, Pieris rapae crucivora, Papilio xuthus, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Cydla pomonella, Helicoverpa armigera, Helicoverpa assulta, Helicoverpa zea, Heliothis virescens, Ostrinia nubilalis, Mamestra brassicae, Mythimna separata, Sesamia inferens, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata,* and *Manduca sexta;*

Hemipteran insects such as *Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Aleurolobus taonabae, Viteus vitifolii, Lipaphis erysimi, Aphis gossypii, Aphis spiraecola, Myzus persicae, Toxoptera aurantii, Drosicha corpulenta, Icerya purchasi, Phenacoccus solani, Pulvinaria aurantii, Planococcus citri, Pseudaonidia duplex, Planococcus kuraunhiae, Pseudococcus comstocki, Comstockaspis perniciosa, Ceroplastes ceriferus, Ceroplastes rubens, Aonidiella aurantii, Fiorinia theae, Pseudaonidia paeoniae, Pseudaulacaspis pentagona, Pseudaulacaspis prunicola, Unaspis euonymi, Unaspis yanonensis, Cimex lectularius, Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus,* and *Trigonotylus caelestialium;*

Coleopteran insects such as *Anomala cuprea, Anomala rufocuprea, Gametis jucunda, Heptophylla picea, Popillia japonica, Lepinotarsa decemlineata, Epilachna varivestis, Melanotus fortnumi, Melanotus tamsuyensis, Lasioderma serricorne, Lyctusbrunneus, Tomicus piniperda, Rhizopertha dominica, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Oulema oryzae, Chaetocnema concinna, Diabrotica undecimpunctata, Diabrotica virgifera, Diabrotica barberi, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus,* and *Paederus fuscipes;*

Thysanopteran insects such as *Frankliniella intonsa, Thrips flavus, Frankliniella occidentalis, Heliothrips haemorrhoidalis, Scirtothrips dorsalis, Thrips palmi, Thrips tabaci,* and *Ponticulothrips diospyrosi;*

Dipterous insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Delia antique, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsitans, Prosimulium yezoensis, Tabanus trigonus, Telmatoscopus albipunctatus, Leptocon-*

*ops nipponensis*, *Culex pipiens pallens*, *Aedes aegypti*, *Aedes albopicutus*, and *Anopheles hyracanus sinesis*;

Hymenopteran insects such as *Apethymus kuri*, *Athalia rosae*, *Arge pagana*, *Neodiprion sertifer*, *Dryocosmus kuriphilus*, *Eciton burchelli*, *Eciton schmitti*, *Camponotus japonicus*, *Vespa mandarina*, *Myrmecia* spp., *Solenopsis* spp., and *Monomorium pharaonic*;

Orthopteran insects such as *Teleogryllus emma*, *Gryllotalpa orientalis*, *Locusta migratoria*, *Oxya yezoensis*, and *Schistocerca gregaria*;

Collembolan insects such as *Onychiurus folsomi*, *Onychiurus sibiricus*, and *Bourletiella hortensis*;

Dictyopteran insects such as *Periplaneta fuliginosa*, *Periplaneta japonica*, *Blattella germanica*, *Periplaneta Americana*, and the like;

Isopterous insects such as *Coptotermes formosanus*, *Reticulitermes speratus*, and *Odontotermes formosanus*;

Isopterous insects such as *Ctenocephalidae felis*, *Ctenocephalides canis*, *Echidnophaga gallinacea*, *Pulex irritans*, and *Xenopsylla cheopis*;

Mallophaga insects such as *Menacanthus stramineus* and *Bovicola bovis*;

Anoplura insects such as *Haematopinus eurysternus*, *Haematopinus suis*, *Linognathus vituli*, and *Solenopotes capillatus*;

Tarsonemidae such as *Phytonemus pallidus*, *Polyphagotarsonemus latus*, and *Tarsonemus bilobatus*;

Eupodidae such as *Penthaleus erythrocephalus* and *Penthaleus major*;

Tetranychidae such as *Oligonychus shinkajii*, *Panonychus citri*, *Panonychus mori*, *Panonychus ulmi*, *Tetranychus kanzawai*, and *Tetranychus urticae*;

Eriophydae such as *Acaphylla theavagrans*, *Aceria tulipae*, *Aculops lycopersici*, *Aculops pelekassi*, *Aculus schlechtendali*, *Eriophyes chibaensis*, and *Phyllocoptruta oleivora*;

Acaridae such as *Rhizoglyphus robini*, *Tyrophagus putrescentiae*, and *Tyrophagus similis*;

Varroidae such as *Varroa jacobsoni*;

Ixodidae such as *Boophilus microplus*, *Rhipicephalus sanguineus*, *Haemaphysalis longicornis*, *Haemophysalis flava*, *Haemophysalis campanulata*, *Ixodes ovatus*, *Ixodes persulcatus*, *Amblyomma* spp., and *Dermacentor* spp.;

Cheyletidae such as *Cheyletiella yasguri* and *Cheyletiella blakei*;

Demodicidae such as *Demodex canis* and *Demodex cati*;

Psoroptidae such as *Psoroptes ovis*;

Sarcoptidae such as *Sarcoptes scabiei*, *Notoedres cati*, *Knemidocoptes* spp., and the like;

Crustacea such as *Armadillidium vulgare*;

Gastropoda such as *Pomacea canaliculata*, *Achatina fulica*, *Meghimatium bilineatum*, *Limax Valentiana*, *Acusta despecta sieboldiana*, and *Euhadra peliomphala*; and Nematoda such as *Prathylenchus coffeae*, *Prathylenchus penetrans*, *Prathylenchus vulnus*, *Globodera rostochiensis*, *Heterodera glycines*, *Meloidogyne hapla*, *Meloidogyne incognita*, *Aphelenchoides besseyi*, and *Bursaphelenchus xylophilus*. However, the insects, the mites, the crustaceans, the molluscs, and the nematodes that can be controlled using an amide derivative represented by Formula (3) according to the invention are not limited thereto.

The pest control agent that includes, as an active ingredient, an amide derivative represented by Formula (3) and produced using the production method according to the invention has a significant effect in terms of control of the above-described harmful crops which damage lowland crops, upland crops, fruit trees, vegetables, other crops, flowers, ornamental plants, and the like. Therefore, the effect as a pest control agent according to the invention can be obtained by treating paddy field water, plant stems/leaves, or soil of a paddy field, dry field, fruit tree, vegetable, another crop, flower, ornamental plant, or the like, in accordance with the period when the occurrence of a pest is expected, before the occurrence of a pest is observed, or at a time point when the occurrence of a pest is observed.

The pest control agent that includes, as an active ingredient, an amide derivative represented by Formula (3) and produced using the production method according to the invention has a significant effect in terms of stored-grain pests and the like that occur during storage of harvest. Specifically, the pest control agent that includes, as an active ingredient, an amide derivative represented by Formula (3) and produced using the method of producing an amide derivative according to the invention may be used for post-harvest treatment on the harvest or a storage place for the harvest, such as spraying, smearing, coating, dipping, dressing, fumigation/smoking, or pressure-injection.

Plant damage caused by pests occurring after seeding can be prevented by applying, to a plant seed, the pest control agent that includes an amide derivative represented by Formula (3) and produced using the production method according to the invention as an active ingredient. Specifically, the pest control agent including, as an active ingredient, an amide derivative represented by Formula (3) and produced using the compound of the invention may be used, in an effective amount for pest control, for treatment on a plant seed such as spraying, smearing, dipping, or dressing, thereby contacting the amide derivative produced using the method according to the invention with the plant seed, wherein the pest control agent may be used for the treatment as it is, or after adequately diluted with water or the like, or in the form of a suspension. The term "plant seed" as used herein refer to an entity that stores nutrients for germination and that is used for breeding in agriculture. Examples thereof include: seeds such as of corn, soybeans, red beans, cotton, rice, sugar beet, wheat, barley, sunflower, tomato, cucumber, eggplant, spinach, sting beans, squash, sugarcane, tobacco, green pepper, and canola; seed tubers such as of taro, potato, sweet potato, and konjac; bulbs such as of edible lily, and tulips; and seed balls such as of shallot.

The pest control agent that includes, as an active ingredient, an amide derivative represented by Formula (3) and produced using the production method according to the invention has a significant effect in terms of controlling hygiene pests including Diptera pests (*Culex pipiens pallens*, *Culex p. molestus*, *Chironomidae*, *Musca domestica*, *Psychodidae*, and *Tabanus trigonus*) and Dictyoptera pests (such as *Blattella germanica*, *Periplaneta fuliginosa*, and *Periplaneta americana*).

The pest control agent that includes, as an active ingredient, an amide derivative represented by Formula (3) and produced using the production method according to the invention has a significant effect in terms of controlling wood-eating pests such as termites, Lyctusbrunneus, *Rhizopertha dominica*, Anobiidae, and Cerambycidae. Therefore, the wood-feeding pests can be controlled by treating soil or wood of buildings or the like with the pest control agent.

The amide derivative represented by Formula (3) and produced using the production method according to the invention exhibits an effect in terms of controlling various pests, and exhibits an excellent control effect as an insecticide or a miticide as well as an effect of protecting useful crops with a small drug amount. Therefore, the amide derivative has an effect of significantly contributing to reduction of environmental loads.

Further, the amide derivative represented by Formula (3) and produced using the method of producing an amide derivative according to the invention offers an excellent control effect even when used in mixture with another agro-horticultural insecticide, a miticide, a nematicide, a germicide, a herbicide, a plant growth regulating agent, a biological agrochemical, or the like.

When the amide derivative represented by Formula (3) and produced using the production method according to the invention is used, the amide derivative is usually mixed with an appropriate solid carrier or liquid carrier, and a surfactant, a penetrating agent, a spreading agent, a thickening agent, an anti-freeze agent, a binding agent, a solidification preventing agent, a disintegrant, a defoamant, a preservative, a degradation preventing agent, and the like are optionally added thereto; the resultant may be used in practical applications as a formulation of an arbitrary dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet, or an emulsifiable gel. Further, the formulation of an arbitrary dosage form may be encapsulated in a water-soluble package such as a water-soluble capsule or a water-soluble film bag, from the viewpoints of labor saving and safety improvement.

An inert carrier that can be used may be in a solid form or a liquid form, and examples of the material that can serve as a solid inert carrier include soybean powder, a cereal powder, a wood powder, a bark powder, a saw powder, a tobacco stalk powder, a walnut shell powder, bran, a cellulose powder, a residue obtained as a result of extraction of a plant extract, a synthetic polymer such as a pulverized synthetic resin, a clay (such as kaolin, bentonite, or acidic white clay), a talc (such as talc or pyrofilide), a silica (such as diatomaceous earth, silica sand, mica, or white carbon (synthetic, highly-dispersed silicic acid, which is also referred to as water-containing micro-silica or water-containing silicic acid, and of which some products contain calcium silicate as a main component)), activated carbon, sulfur powder, pumice, calcined diatomaceous earth, ground brick, fly ash, sand, inorganic mineral powder such as of calcium carbonate or calcium phosphate, chemical fertilizers such as ammonium sulfate, ammonium phosphate, ammonium nitrate, urea, or ammonium chloride, and compost. These are used singly, or in mixture of two or more thereof.

The material that can be used as a liquid inert carrier is selected from materials that intrinsically have solvent power, and materials which do not have solvent power and in which the active ingredient compound can be dispersed when assisted by an auxiliary agent. Representative examples of the carrier, which may be used singly or in mixture of two or more thereof, include the following: water, alcohols (such as methanol, ethanol, isopropanol, butanol, and ethylene glycol), ketones (such as acetone, methyl ethyl ketone, methyl isobutyl ketone, diisobutyl ketone, and cyclohexanone), ethers (such as diethyl ether, dioxane, cellosolve, diisopropyl ether, and tetrahydrofuran), aliphatic hydrocarbons (such as kerosine and mineral oil), aromatic hydrocarbons (such as benzene, toluene, xylene, solvent naphtha, and alkylnaphthalene), halogenated hydrocarbons (such as dichloromethane, chloroform, carbon tetrachloride, and chlorobenzene), esters (such as ethyl acetate, butyl acetate, ethyl propionate, diisobutyl phthalate, dibutyl phthalate, and dioctyl phthalate), amides (such as dimethylformamide, diethylformamide, and dimethylacetamide), and nitriles (such as acetonitrile). These solid and liquid carriers may be used singly, or in combination of two or more thereof.

Examples of the surfactant include: nonionic surfactants such as polyoxyethylene alkyl ether, polyoxyethylene alkyl (mono- or di-)phenyl ether, polyoxyethylene (mono-, di-, or tri-)styryl phenyl ether, polyoxyethylene polyoxypropylene block copolymer, polyoxyethylene fatty acid (mono- or di-) ester, sorbitan fatty acid ester, polyoxyethylene sorbitan fatty acid ester, castor oil ethylene oxide adduct, acetylene glycol, acetylene alcohol, ethylene oxide adduct of acetylene glycol, ethylene oxide adduct of acetylene alcohol, and alkyl glycosides; anionic surfactants such as alkyl sulfate salts, alkyl benzenesulfonates, lignin sulfonates, alkyl sulfosuccinates, naphthalenesulfonates, alkyl naphthalenesulfonates, salts of formalin condensates of naphthalenesulfonic acid, salts of formalin condensates of alkyl naphthalenesulfonic acid, polyoxyethylene alkyl ether sulfuric ester salts, polyoxyethylene alkyl ether phosphoric ester salts, polyoxyethylene (mono- or di-)alkyl phenyl ether sulfuric ester salts, polyoxyethylene (mono- or di-)alkyl phenyl ether phosphoric ester salts, polyoxyethylene (mono-, di- or tri-)styryl phenyl ether sulfuric ester salts, polyoxyethylene (mono-, di- or tri-)styryl phenyl ether phosphoric ester salts, polycarbonates (such as polyacrylates, polymaleates, and copolymers of maleic acid and olefins), and polystyrenesulfonates; cationic surfactants such as alkylamine salts and alkyl quaternary ammonium salts; amphoteric surfactants such as of amino acid type or betaine type; silicon-based surfactants; and fluorocarbon surfactants.

There are no particular limitations on the content of surfactants, such as those described above. The content of surfactants is usually preferably in the range of from 0.05 parts by weight to 20 parts by weight with respect to 100 parts by weight of the formulation of the invention. Further, the surfactant may be used singly, or in combination of two or more thereof.

In order to control various pests, the amide derivative represented by Formula (3) may be applied, in an amount effective for disease control, to crops in which occurrence of a pest is expected, or to a place at which occurrence of a pest is undesired, wherein the amide derivative may be applied as it is, or after appropriately diluted with water or the like, or in a suspended form. The amount of the amide derivative to be used may vary with various factors such as the purpose, subject pest, the growth conditions of the crop, the tendency of occurrence of pests, climate, environmental conditions, dosage form, method of application, place of application, and the timing of application. The amide derivative may be used at an active ingredient concentration of preferably 0.0001 ppm to 5000 ppm, and more preferably 0.01 ppm to 1000 ppm. Further, the amount of the active ingredient to be applied per 10 acre is generally 1 g to 300 g.

The amount of the active ingredient of the amide derivative represented by Formula (3) and produced using the production method according to the invention is usually from 0.1% by weight to 20% by weight in a dustable powder, from 5% by weight to 50% by weight in an emulsion formulation, from 3% by weight to 90% by weight in a wettable powder, from 0.1% by weight to 20% by weight in a granule, from 5% by weight to 90% by weight in a flowable formulation, and from 3% by weight to 90% by weight in a water dispersible granule. In regard to the amount of carrier in each dosage form, the amount of carrier is usually from 60% by weight to 99.9% by weight in a dustable powder, from 40% by weight to 95% by weight in an emulsifiable concentrate, from 10% by weight to 90% by weight in a wettable powder, from 80% by weight to 99.9% by weight in a granule, from 10% by weight to 95% by weight in a flowable formulation, and from 10% by weight to 90% by weight in a water dispersible granule. Further, the amount of the auxiliary agent is usually from 0.1% by weight to 20% by weight in a dustable powder, from 1% by weight to 20% by weight in an emulsion formulation, from 0.1% by weight to 20% by weight in a wettable powder, from 0.1% by weight to 20% by weight in a granule, from 0.1% by weight to 20% by weight in a flowable formulation, and from 0.1% by weight to 20% by weight in a wettable granule.

Further, in a case in which the compound according to the invention is used as an agrochemical, the compound according to the invention to be used may be mixed with other herbicides, various insecticides, miticides, nematocides, germicides, plant growth regulating agents, synergists, fertilizers, soil improving agents, and the like during the production of the formulation or at the time of spreading.

The disclosure of Japanese Patent Application No. 2008-208714 is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

EXAMPLES

Representative embodiments according to the invention are described below by reference to the following Examples. However, the invention is not limited thereto. $^1$H-NMR spectrum is reported in ppm toward lower magnetic field from tetramethylsilane, in which "s" means singlet, "d" means doublet, "t" means triplet, "m" means muliplet, "dd" means a double doublet, and "brs" means a broad singlet.

Example 1

Production of methyl 2-fluoro-3-(N-methylbenzamido)benzoate (Compound No. 1-2)

Step 1

Production of methyl 2-chloro-3-nitrobenzoate

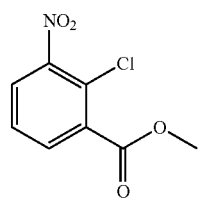

2-chloro-3-nitrobenzoic acid (543.6 g, 2.7 mol) was suspended in methanol (3425.0 ml), and concentrated sulfuric acid (108.5 ml) was added thereto. The mixture was heated to reflux for 6 hours. The mixture was cooled to room temperature, and then the solvent was concentrated under reduced pressure. The concentration residue was added into a saturated aqueous solution of sodium bicarbonate. A solid that precipitated was filtered, and washed with water. The solid thus obtained was dissolved in ethyl acetate, washed with saturated saline, and then dried over anhydrous sodium sulfate. The sodium sulfate was filtered away, the filtrate was concentrated and dried to solid under reduced pressure, and the resultant solid was washed with n-hexane. As a result, 542.6 g (yield: 93%) of the indicated compound was obtained $^1$H-NMR (CDCl$_3$, ppm) δ 3.98 (3H, s), 7.46-7.50 (1H, m), 7.83-7.86 (1H, m), 7.94-7.98 (1H, m).

Step 2

Production of methyl 2-fluoro-3-nitrobenzoate

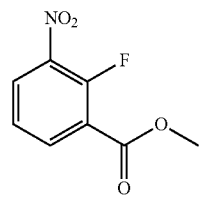

Cesium fluoride (499.02 g, 3.19 mol) was added into a flask equipped with a stirrer under a nitrogen gas stream, and was agitated for one hour at 110° C. Methyl 2-chloro-3-nitrobenzoate (229.00 g, 1.06 mol) and N,N-dimethylformamide (2000 ml) were added thereto, and the reaction mixture was agitated for one hour at 140° C. The reaction mixture was naturally cooled to room temperature, and then was filtered, and the filtrate was concentrated under reduced pressure. The concentration residue was poured into water and agitated for a while, and then a solid that precipitated was collected by filtration and dried under reduced pressure. As a result, 160.03 g (yield: 76%) of the indicated compound was obtained.

$^1$H-NMR (CDCl$_3$, ppm) δ 3.99 (3H, s), 7.36-7.40 (1H, m), 8.14-8.25 (2H, m).

Step 3

Production of methyl 3-amino-2-fluorobenzoate hydrochloride

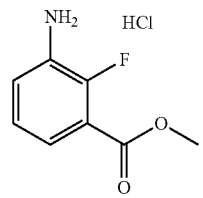

2-Fluoro-3-nitrobenzoic acid methyl ester (9.10 g, 0.046 mol), 10% hydrochloric acid/methanol (25 ml), methanol (60 ml), and 5% palladium/carbon (50% wet product) (2.7 g) were introduced, and the reaction mixture was hydrogenated at room temperature. After completion of the reaction, the catalyst was filtered away, and the filtrate was concentrated under reduced pressure. The concentration residue was washed with diisopropyl ether, as a result of which 8.01 g (yield: 85%) of the indicated compound was obtained.

$^1$H-NMR (DMSO-d$_6$, ppm) δ 3.86 (3H, s), 7.21-7.25 (1H, m), 7.27 (3H, brs), 7.42-7.53 (2H, m).

Step 4

Production of methyl 3-benzamido-2-fluorobenzoate (Compound No. 1-1)

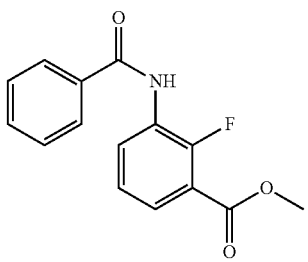 [SMILES: COC(=O)c1cccc(NC(=O)c2ccccc2)c1F]

Methyl 3-amino-2-fluorobenzoate hydrochloride (7.77 g, 0.037 mol) was suspended in methylene chloride (100 ml), and pyridine (6.94 g, 0.085 mol) was added dropwise thereto. Benzoyl chloride (5.78 g, 0.041 mol) was added dropwise to this reaction mixture under cooling, and the mixture was agitated overnight at room temperature. After completion of the reaction, the reaction mixture was washed sequentially with a 1N hydrochloric acid, a saturated aqueous solution of sodium bicarbonate, and saturated saline, and the reaction mixture was dried over anhydrous sodium sulfate. The sodium sulfate was filtered away, and then the filtrate was concentrated under reduced pressure. The concentration residue was recrystallized from ethyl acetate, as a result of which 8.79 g (yield: 85%) of the indicated compound was obtained.

$^1$H-NMR (CDCl$_3$, ppm) δ 3.95 (3H, s), 7.24-7.28 (1H, m), 7.51-7.58 (3H, m), 7.66-7.70 (1H, m), 7.89-7.91 (2H, m), 8.20-8.22 (1H, m), 8.70-8.73 (1H, m).

Step 5

Synthesis of methyl 2-fluoro-3-(N-methylbenzamido)benzoate (Compound No. 1-2)

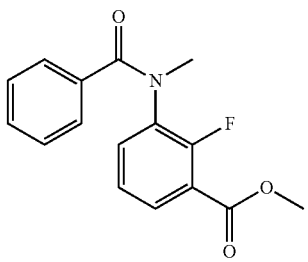 [SMILES: COC(=O)c1cccc(N(C)C(=O)c2ccccc2)c1F]

Methyl 3-benzamido-2-fluorobenzoate (8.75 g, 32.0 mmol) was dissolved in acetonitrile (200 ml). Dimethyl sulfate (4.3 g, 34.1 mmol) and potassium hydroxide (2.63 g, 39.8 mmol) were sequentially added thereto, and the reaction mixture was agitated for 30 minutes at 60° C. The mixture was cooled to room temperature, and then was concentrated. Ethyl acetate was added to the concentration residue, and the mixture was washed with water and dried over anhydrous sodium sulfate. The sodium sulfate was filtered away, and the filtrate was concentrated under reduced pressure. n-hexane was added to the concentration residue, as a result of which 8.00 g (yield: 87%) of the indicated compound was obtained.

$^1$H-NMR (CDCl$_3$, ppm) δ 3.43 (3H, s), 3.90 (3H, s), 7.01-7.05 (1H, m), 7.20-7.33 (6H, m), 7.77-7.79 (1H, m).

Example 2

Production of 2-fluoro-3-(N-methylbenzamido)benzoyl chloride (Compound No. 2-5)

Step 1

Synthesis of methyl 2-fluoro-3-(methylamino)benzoate

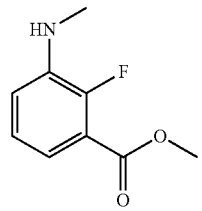

Methyl 3-amino-2-fluorobenzoate hydrochloride (18.65 g, 0.09 mol) was dissolved in a 37% formalin solution. While maintaining the temperature at 40° C. or lower, 98% sulfuric acid (680.81 g, 6.80 mol) was added dropwise thereto. Thereafter, the mixture was naturally cooled, and agitated for 2 hours at room temperature. The reaction mixture was poured into ice water, and was neutralized with sodium bicarbonate. The neutralized liquid was filtered, and washed with ethyl acetate. Then, the filtrate was extracted, and dried over anhydrous sodium sulfate. The sodium sulfate was filtered away, and then the concentration residue was purified by silica gel column chromatography (developer solvent: ethyl acetate/n-hexane=1/4), as a result of which 6.27 g (yield: 38%) of the indicated compound was obtained.

$^1$H-NMR (CDCl$_3$, ppm) δ 2.89 (3H, s), 3.91 (3H, s), 6.80-6.85 (1H, m), 7.03-7.09 (1H, m), 7.14-7.16 (2H, m).

Step 2

Synthesis of methyl 2-fluoro-3-(N-methylbenzamido)benzoate (Compound No. 1-2)

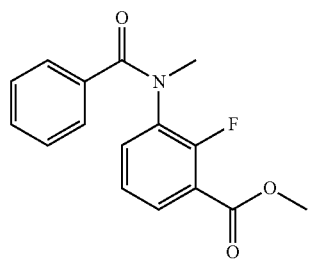 [SMILES: COC(=O)c1cccc(N(C)C(=O)c2ccccc2)c1F]

2-Fluoro3-(methylamino)benzoic acid (1.42 g, 4.94 mmol) was dissolved in tetrahydrofuran (15 ml), and benzoyl chloride (0.83 g, 5.90 mmol) and pyridine (0.47 g, 5.94 mmol) were added thereto. The reaction mixture was allowed to react for 12 hours at room temperature. Ethyl acetate was added to the reaction solution, and the mixture was washed sequentially with water, a 1N hydrochloric acid, a saturated aqueous solution of sodium bicarbonate, and saturated saline, and then dried over anhydrous sodium sulfate. The sodium sulfate was filtered away, and the concentration residue was purified by silica gel column chromatography (developer solvent: ethyl acetate/n-hexane=1/8), as a result of which 1.42 g (yield: 64%) of the indicated compound was obtained.

$^1$H-NMR (CDCl$_3$, ppm) δ 3.43 (3H, s), 3.92 (3H, s), 7.01-7.05 (1H, m), 7.19-7.32 (6H, m), 7.76-7.79 (1H, m).

Step 3

Synthesis of 2-fluoro-3-(N-methylbenzamido)benzoic acid (Compound No. 1-3)

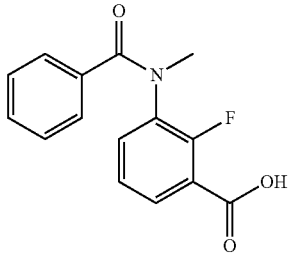 [SMILES: CN(C(=O)c1ccccc1)c1cccc(C(=O)O)c1F]

Sodium hydroxide (0.26 g, 6.50 mmol) was dissolved in methanol (30 ml), and methyl 2-fluoro-3-(N-methylbenzamido)benzoate (1.42 g, 4.94 mmol) was added thereto. The mixture was heated for 3 hours at 60° C. The mixture was cooled to room temperature, and then the solvent was concentrated under reduced pressure. The concentration residue was dissolved in water, and washed with methylene chloride. While the aqueous layer was cooled, the pH thereof was adjusted to 2 to 3 with a 1N hydrochloric acid, and a solid precipitated during continued agitation. The resultant solid was filtered, washed with water, and dried at 50° C., as a result of which 1.25 g (yield: 94%) of the indicated compound was obtained.

$^1$H-NMR (CDCl$_3$, ppm) δ 3.45 (3H, s), 7.05-7.09 (1H, m), 7.21-7.35 (6H, m), 7.85-7.90 (1H, m), 10.29 (1H, brs).

Step 4

Production of 2-fluoro-3-(N-methylbenzamido)benzoyl chloride (Compound No. 2-5)

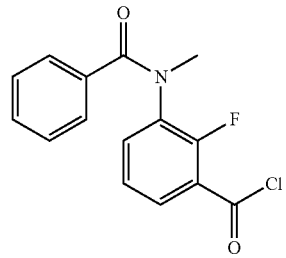 [SMILES: CN(C(=O)c1ccccc1)c1cccc(C(=O)Cl)c1F]

2-Fluoro-3-(N-methylbenamido)benzoic acid (3.0 g, 11.0 mmol) was suspended in toluene (35 ml). Thionyl chloride (4.9 ml, 66 mmol) was added to the suspension, and the mixture was heated to reflux for one hour. The mixture was cooled to room temperature, and then the solvent was concentrated under reduced pressure. As a result, 3.21 g (quantitative) of the indicated compound was obtained.

$^1$H-NMR (CDCl$_3$, ppm) δ 3.17 (3H, s), 7.15 (1H, t, J=8.0 Hz), 7.23-7.35 (6H, m), 7.94 (1H, t, J=8.0 Hz).

Example 3

Production of 2-fluoro-3-(4-fluoro-N-methylbenzamido)benzoyl chloride (Compound No. 2-15)

Step 1

Production of methyl 2-fluoro-3-(4-fluorobenzamido)benzoate (Compound No. 1-20)

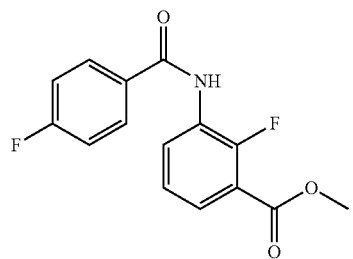 [SMILES: COC(=O)c1cccc(NC(=O)c2ccc(F)cc2)c1F]

The indicated compound was obtained from methyl 3-amino-2-fluorobenzoate hydrochloride and p-fluorobenzoyl chloride, in a manner similar to the (Step 4) of Example 1.

$^1$H-NMR (CDCl$_3$, ppm) δ 3.95 (3H, s), 7.17-7.27 (3H, m), 7.66-7.70 (1H, m), 7.89-7.94 (2H, m), 8.11 (1H, brs), 8.63-8.68 (1H, m).

Step 2

Production of methyl 2-fluoro-3-(4-fluoro-N-methylbenzamido)benzoate (Compound No. 1-21)

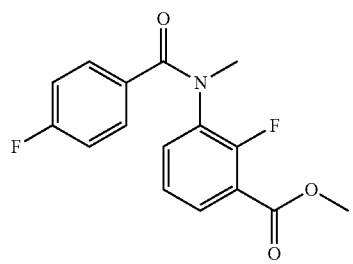 [SMILES: COC(=O)c1cccc(N(C)C(=O)c2ccc(F)cc2)c1F]

The indicated compound was obtained from methyl 2-fluoro-3-(4-fluorobenzamido)benzoate and dimethyl sulfate, in a manner similar to the (Step 5) of Example 1.

$^1$H-NMR (CDCl$_3$, ppm) δ 3.42 (3H, s), 3.88 (3H, s), 6.86-6.90 (2H, m), 7.09-7.13 (1H, m), 7.32-7.38 (3H, m), 7.78-7.82 (1H, m).

Step 3

Production of 2-fluoro-3-(4-fluoro-N-methylbenzamido)benzoic acid (Compound No. 1-22)

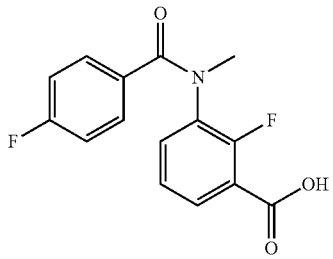 [SMILES: CN(C(=O)c1ccc(F)cc1)c1cccc(C(=O)O)c1F]

The indicated compound was obtained from methyl 2-fluoro-3-(4-fluoro-N-methylbenzamido)benzoate, in a manner similar to the (Step 3) of Example 2.
$^1$H-NMR (CDCl$_3$, ppm) δ 3.45 (3H, s), 6.87-6.91 (2H, m), 7.10-7.18 (1H, m), 7.30-7.37 (3H, m), 7.87-7.92 (1H, m); the proton of carboxylic acid was not detected.

Step 4

Production of 2-fluoro-3-(4-fluoro-N-methylbenzamido)benzoyl chloride (Compound No. 2-15)

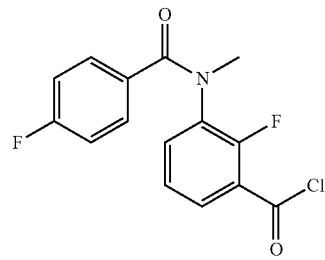 [SMILES: CN(C(=O)c1ccc(F)cc1)c1cccc(C(=O)Cl)c1F]

The indicated compound was obtained from 2-fluoro-3-(4-fluoro-N-methylbenzamido)benzoic acid and thionyl chloride, in a manner similar to the (Step 4) of Example 2.
$^1$H-NMR (CDCl$_3$, ppm) δ 2.95 (3H, s), 6.92 (2H, t, J=8.8 Hz), 7.19 (1H, t, J=8.0 Hz), 7.33-7.36 (3H, m), 7.97 (1H, t, J=8.0 Hz).

Example 4

Production of 2-fluoro-3-(3-fluoro-N-methylbenzamido)benzoic acid (Compound 1-65)

Step 1

Production of methyl 2-fluoro-3-(3-fluorobenzamido)benzoate (Compound No. 1-63)

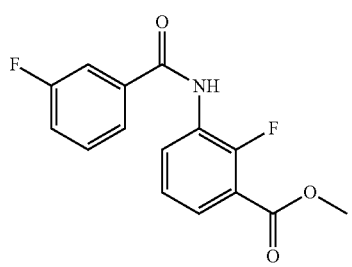 [SMILES: COC(=O)c1cccc(NC(=O)c2cccc(F)c2)c1F]

The indicated compound was obtained from methyl 3-amino-2-fluorobenzoate hydrochloride and 3-fluorobenzoyl chloride, in a manner similar to the (Step 4) of Example 1.
$^1$H-NMR (CDCl$_3$, ppm) δ 3.95 (3H, s), 7.24-7.30 (2H, s), 7.48-7.54 (1H, m), 7.61-7.72 (3H, m), 8.10 (1H, brs), 8.68-8.70 (1H, m).

Step 2

Production of methyl 2-fluoro-3-(3-fluoro-N-methylbenzamido)benzoate (Compound No. 1-64)

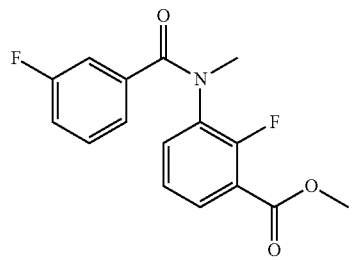 [SMILES: COC(=O)c1cccc(N(C)C(=O)c2cccc(F)c2)c1F]

The indicated compound was obtained from methyl 2-fluoro-3-(3-fluorobenzamido)benzoate and dimethyl sulfate, in a manner similar to the (Step 5) of Example 1.
$^1$H-NMR (CDCl$_3$, ppm) δ 3.46 (3H, s), 3.93 (3H, s), 6.95-7.22 (6H, m), 7.79-7.82 (11-1, m).

Step 3

Production of 2-fluoro-3-(3-fluoro-N-methylbenzamido)benzoic acid (Compound No. 1-65)

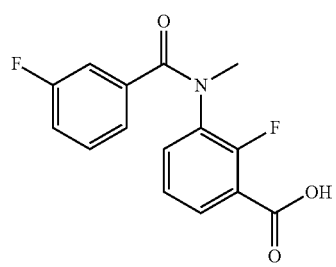 [SMILES: CN(C(=O)c1cccc(F)c1)c1cccc(C(=O)O)c1F]

The indicated compound was obtained from methyl 2-fluoro-3-(3-fluoro-N-methylbenzamido)benzoate, in a manner similar to the (Step 3) of Example 2.
$^1$H-NMR (CDCl$_3$, ppm) δ 3.44 (3H, s), 6.98-7.00 (1H, m), 7.07-7.16 (4H, m), 7.29-7.30 (1H, m), 7.88-7.91 (1H, m); the proton of carboxylic acid was not detected.

Example 5

Production of 3-(N-ethylbenzamido)-2-fluorobenzoic acid (Compound No. 1-11)

Step 1

Production of methyl 3-(N-ethylbenzamido)-2-fluorobenzoate (Compound No. 1-10)

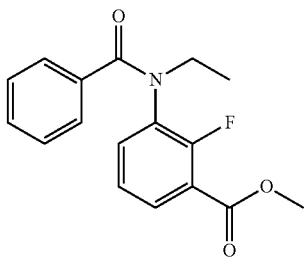 [SMILES: CCN(C(=O)c1ccccc1)c1cccc(C(=O)OC)c1F]

Methyl 3-benzamido-2-fluorobenzoate (3.10 g, 11.0 mmol) was dissolved in N,N-dimethylformamide (30 ml), and the solution was cooled. 60% Sodium hydride (0.53 g, 13.2 mmol) was added thereto, and the reaction mixture was agitated without heating or cooling. 10 minutes later, ethyl iodide (2.05 g, 13.0 mmol) was added to the mixture, and the mixture was agitated overnight at room temperature. Water was added dropwise to the reaction mixture, and the reaction mixture was extracted with ethyl acetate, and dried over anhydrous sodium sulfate. The sodium sulfate was filtered away, and then the filtrate was concentrated under reduced pressure. The concentration residue was purified by silica gel column chromatography (developer solvent: ethyl acetate/n-hexane=1/5), as a result of which 2.03 g (yield: 61%) of the indicated compound was obtained.

$^1$H-NMR (CDCl$_3$, ppm) δ 1.19-1.28 (3H, m), 3.88-4.04 (5H, m), 7.06-7.30 (7H, m), 7.80-7.83 (1H, m).

Step 2

Production of 3-(N-ethylbenzamido)-2-fluorobenzoic acid (Compound No. 1-11)

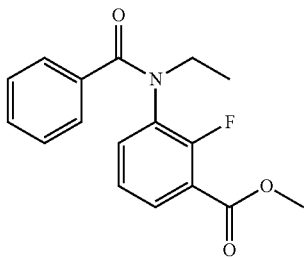 [SMILES: CCN(C(=O)c1ccccc1)c1cccc(C(=O)OC)c1F]

The indicated compound was obtained by hydrolyzing methyl 3-(N-ethylbenzamido)-2-fluorobenzoate, in a manner similar to the (Step 3) of Example 2.

$^1$H-NMR (DMSO-d$_6$, ppm) δ 1.08-1.19 (3H, m), 3.74-3.89 (2H, m), 7.24-7.40 (6H, m), 7.64-7.73 (2H, m), 13.36 (1H, brs).

Example 6

Production of 2-fluoro-3-(N-n-propylbenzamido)benzoic acid (Compound No. 1-13)

Step 1

Production of methyl 2-fluoro-3-(N-n-propylbenzamido)benzoate (Compound No. 1-12)

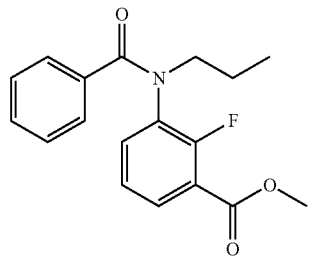 [SMILES: CCCN(C(=O)c1ccccc1)c1cccc(C(=O)OC)c1F]

The indicated compound was obtained from methyl 3-benzamido-2-fluorobenzoate and n-propyl iodide, in a manner similar to the (Step 5) of Example 1.

$^1$H-NMR (CDCl$_3$, ppm) δ 0.92-1.02 (3H, m), 1.59-1.63 (2H, m), 3.72-3.78 (2H, m), 3.09 (3H, s), 7.05-7.06 (1H, m), 7.18-7.28 (6H, m), 7.70-7.71 (1H, m).

Step 2

Production of 2-fluoro-3-(N-n-propylbenzamido)benzoic acid (Compound No. 1-13)

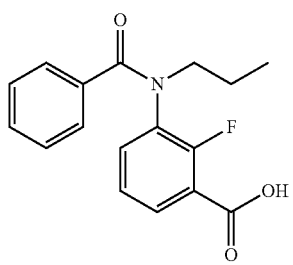 [SMILES: CCCN(C(=O)c1ccccc1)c1cccc(C(=O)O)c1F]

The indicated compound was obtained by hydrolyzing methyl 3-(N-n-propylbenzamido)-2-fluorobenzoate, in a manner similar to the (Step 3) of Example 2.

$^1$H-NMR (CDCl$_3$+DMSO-d$_6$, ppm) δ 0.88-0.94 (3H, m), 1.60-1.65 (2H, m), 3.72-3.73 (1H, m), 3.91-3.92 (1H, m), 7.04-7.06 (1H, m), 7.22-7.28 (6H, m), 7.79-7.80 (1H, m); the proton of carboxylic acid was not detected.

Example 7

Production of 3-(2-chloro-4-fluoro-N-methylbenzamido)-2-fluorobenzoic acid (Compound No. 1-139)

Step 1

Production of methyl 3-(2-chloro-4-fluorobenzamido)-2-fluorobenzoate (Compound No. 1-137)

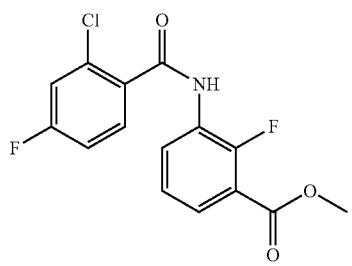 [SMILES: COC(=O)c1cccc(NC(=O)c2ccc(F)cc2Cl)c1F]

The indicated compound was obtained from methyl 3-amino-2-fluorobenzoate hydrochloride and 2-chloro-4-fluorobenzoyl chloride, in a manner similar to the (Step 4) of Example 1.

¹H-NMR (CDCl₃, ppm) δ 3.95 (3H, s), 7.11-7.16 (1H, m), 7.22-7.28 (2H, m), 7.68-7.72 (1H, m), 7.89-7.92 (1H, m), 8.45 (1H, brs), 8.69 (1H, t, J=7.8 Hz).

Step 2

Production of methyl 3-(2-chloro-4-fluoro-N-methylbenzamido)-2-fluorobenzoate (Compound No. 1-138)

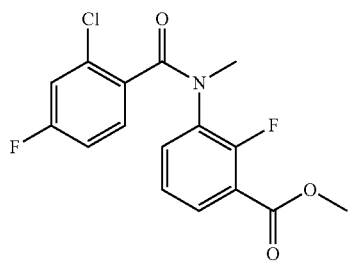 [SMILES: COC(=O)c1cccc(N(C)C(=O)c2ccc(F)cc2Cl)c1F]

The indicated compound was obtained from methyl 3-(2-chloro-4-fluorobenzamido)-2-fluorobenzoate and dimethyl sulfate, in a manner similar to the (Step 5) of Example 1.

¹H-NMR (CDCl₃, ppm) δ 3.44 (3H, s), 3.92 (3H, s), 6.80-6.84 (1H, m), 6.93 (1H, dd, J=2.0, 7.3 Hz), 7.04 (1H, t, J=7.8 Hz), 7.21-7.25 (1H, m), 7.37 (1H, t, J=7.3 Hz), 7.76-7.80 (1H, m).

Step 3

Production of 3-(2-chloro-4-fluoro-N-methylbenzamido)-2-fluorobenzoic acid (Compound No. 1-139)

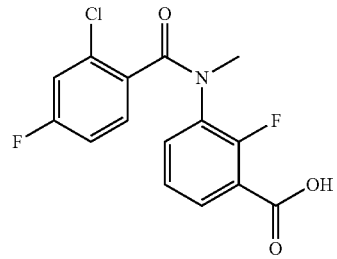 [SMILES: CN(C(=O)c1ccc(F)cc1Cl)c1cccc(C(=O)O)c1F]

The indicated compound was obtained by hydrolyzing methyl 3-(2-chloro-4-fluoro-N-methylbenzamido)-2-fluorobenzoate, in a manner similar to the (Step 3) of Example 2.

¹H-NMR (CDCl₃, ppm) δ 3.46 (3H, s), 5.70 (1H, brs), 6.82-6.86 (1H, m), 6.94 (1H, dd, J=2.4, 8.8 Hz), 7.08 (1H, t, J=7.8 Hz), 7.22-7.28 (1H, m), 7.47-7.48 (1H, m), 7.84-7.88 (1H, m).

Example 8

Production of 3-(4-cyano-N-methylbenzamido)-2-fluorobenzoic acid (Compound No. 1-104)

Step 1

Production of methyl 3-(4-cyanobenzamido)-2-fluorobenzoate (Compound No. 1-102)

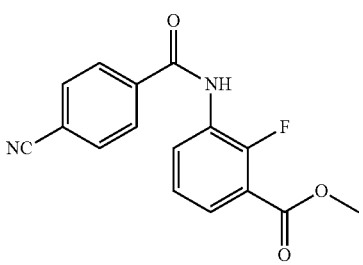 [SMILES: COC(=O)c1cccc(NC(=O)c2ccc(C#N)cc2)c1F]

The indicated compound was obtained from methyl 3-amino-2-fluorobenzoate hydrochloride and 4-cyanobenzoyl chloride, in a manner similar to the (Step 4) of Example 1.

¹H-NMR (DMSO-d₆, ppm) δ 3.88 (3H, s), 7.36 (1H, t, J=7.8 Hz), 7.75-7.79 (1H, m), 7.87-7.91 (1H, m), 8.03-8.10 (2H, m), 8.13-8.15 (2H, m), 10.53 (1H, s).

Step 2

Production of methyl 3-(4-cyano-N-methylbenzamido)-2-fluorobenzoate (Compound No. 1-103)

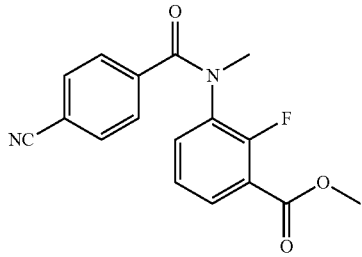 [SMILES: COC(=O)c1cccc(N(C)C(=O)c2ccc(C#N)cc2)c1F]

The indicated compound was obtained from methyl 3-(4-cyanobenzamido)-2-fluorobenzoate and dimethyl sulfate, in a manner similar to the (Step 5) of Example 1.

$^1$H-NMR (CDCl$_3$, ppm) δ 3.44 (3H, s), 3.92 (3H, s), 7.08-7.12 (1H, m), 7.25 (1H, brs), 7.41-7.43 (2H, m), 7.49-7.51 (2H, m), 7.81-7.84 (1H, s).

Step 3

Production of 3-(4-cyano-N-methylbenzamido)-2-fluorobenzoic acid (Compound No. 1-104)

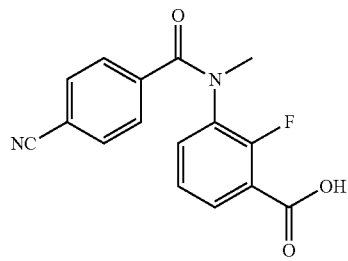 [SMILES: CN(C(=O)c1ccc(C#N)cc1)c1cccc(C(=O)O)c1F]

The indicated compound was obtained by hydrolyzing methyl 3-(4-cyano-N-methylbenzamido)-2-fluorobenzoate, in a manner similar to the (Step 3) of Example 2.

$^1$H-NMR (DMSO-d$_6$, ppm) δ 3.33 (3H, s), 7.22 (1H, brs), 7.45 (2H, brs), 7.69-7.74 (4H, brs); the proton of carboxylic acid was not detected.

Example 9

Production of N-(2-bromo-4-(perfluoropropan-2-yl)-6-(trifluoromethyl)phenyl)-2-fluoro-3-(N-methylbenzamido)benzamide (Compound No. 3-1)

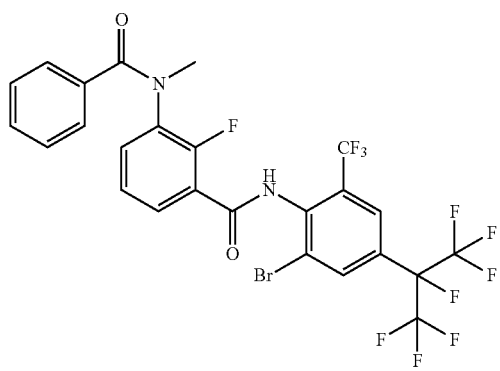 [SMILES: CN(C(=O)c1ccccc1)c1cccc(C(=O)Nc2c(Br)cc(C(F)(C(F)(F)F)C(F)(F)F)cc2C(F)(F)F)c1F]

2-Fluoro-3-(N-methylbenzamido)benzoic acid (5.5 g, 0.02 mol) was suspended in toluene, and thionyl chloride (11.90 g, 0.10 mol) was added thereto. The mixture was agitated for one hour at 100° C. Toluene was concentrated under reduced pressure, and the concentration residue was dissolved in 1,3-dimethyl-2-imidazolidinone (5.0 g). 2-Bromo-4-(perfluoropropan-2-yl)-6-(trifluoromethyl)aniline (6.80 g, 0.017 mol) was added to the solution, and the mixture was agitated for 8 hours at 100° C. The mixture was cooled to room temperature, and then ethyl acetate was added thereto. The mixture was washed sequentially with a saturated aqueous solution of sodium bicarbonate and saturated saline, and was dried over anhydrous sodium sulfate. The sodium sulfate was filtered away, and then the filtrate was concentrated under reduced pressure. The concentration residue was purified by silica gel column chromatography (developer liquid: ethyl acetate/n-hexane=1/3), as a result of which 4.87 (yield: 45%) of the indicated compound, which is an amide derivative represented by Formula (3), was obtained.

$^1$H-NMR (CDCl$_3$, ppm) δ 3.50 (3H, s), 6.99-7.33 (6H, m), 7.43-7.45 (1H, m), 7.90 (1H, s), 7.97-8.06 (2H, m), 8.13 (1H, s).

Example 10

According to the method described in Example 9, the reaction between 2-fluoro-3-(N-methylbenzamido)benzoic acid and 2-bromo-4-(perfluoropropan-2-yl)-6-(trifluoromethyl)aniline was carried out using toluene instead of 1,3-dimethyl-2-imidazolidinone. The indicated compound of Example 9 was obtained at a yield of 14%.

Example 11

According to the method described in Example 9, the reaction between 2-fluoro-3-(N-methylbenzamido)benzoic acid and 2-bromo-4-(perfluoropropan-2-yl)-6-(trifluoromethyl)aniline was carried out using dioxane instead of 1,3-dimethyl-2-imidazolidinone. The indicated compound of Example 9 was obtained at a yield of 16%.

Example 12

According to the method described in Example 9, the reaction between 2-fluoro-3-(N-methylbenzamido)benzoic acid and 2-bromo-4-(perfluoropropan-2-yl)-6-(trifluoromethyl)aniline was carried out in a solvent-free manner without using 1,3-dimethyl-2-imidazolidinone. The indicated compound of Example 9 was obtained at a yield of 37%.

Examples 13 to 19

Corresponding amide derivatives represented by Formula (3) were obtained in the same manner as in Example 9, except that the compounds indicated in the following Table 4 were used instead of 2-fluoro-3-(N-methylbenzamido)benzoic acid (as a compound represented by Formula (2)) and 2-bromo-4-(perfluoropropan-2-yl)-6-(trifluoromethyl)aniline (as a compound represented by Formula (1)).

TABLE 4

| | Compound No. | Compound represented by Formula (2) | Compound represented by Formula (1) | ¹H-NMR |
|---|---|---|---|---|
| Example 13 | 3-6 | 2-fluoro-3-(N-methylbenzamido)benzoic acid | 2-bromo-4-(perfluorobutane-2-yl)-6-(trifluoromethyl)aniline | (CDCl$_3$, ppm)δ3.50(3H, s), 7.23-7.26(2H, m), 7.27-7.32(4H, m), 7.44-7.45(1H, m), 7.88(1H, s), 7.98(1H, t, J = 6.8 Hz), 8.04-8.08(1H, m), 8.11(1H, s). |
| Example 14 | 3-7 | 2-fluoro-3-(N-methylbenzamido)benzoic acid | 2-iodo-4-(perfluoropropan-2-yl)-6-(trifluoromethyl)aniline | (CDCl$_3$, ppm)δ3.51(3H, s), 7.22-7.33(6H, m), 7.44-7.48(1H, m), 7.93(1H, s), 7.99-8.02(2H, m), 8.33(1H, s). |
| Example 15 | 3-23 | 2-fluoro-3-(4-fluoro-N-methylbenzamido)benzoic acid | 2-iodo-4-(perfluoropropan-2-yl)-6-(trifluoromethyl)aniline | (CDCl$_3$, ppm)δ3.50(3H, s), 6.91(2H, t, J = 8.0 Hz), 7.26-7.31(2H, m), 7.33(1H, brs), 7.45-7.49(1H, m), 7.93(1H, s), 8.02-8.05(2H, m), 8.34(1H, s). |
| Example 16 | 3-21 | 2-fluoro-3-(4-fluoro-N-methylbenzamido)benzoic acid | 2-bromo-4-(perfluoropropan-2-yl)-6-(trifluoromethyl)aniline | (CDCl$_3$, ppm)δ3.50(3H, s), 6.91(2H, t, J = 8.0 Hz), 7.26-7.31(2H, m), 7.35(1H, brs), 7.43-7.47(1H, m), 7.90(1H, s), 8.00-8.04(2H, m), 8.13(1H, s). |
| Example 17 | 3-34 | 2-fluoro-3-(3-fluoro-N-methylbenzamido)benzoic acid | 2-iodo-4-(perfluoropropan-2-yl)-6-(trifluoromethyl)aniline | (CDCl$_3$, ppm)δ3.51(3H, s), 7.00-7.17(4H, m), 7.26-7.32(1H, m), 7.45-7.47(1H, m), 7.93(1H, s), 8.02-8.06(2H, m), 8.34(1H, s). |
| Example 18 | 3-19 | (N-methylbenzamido)benzoic acid | 2-iodo-4-(perfluoropropan-2-yl)-6-(trifluoromethyl)aniline | (CDCl$_3$, ppm)δ3.57(3H, s), 7.18-7.23(3H, m), 7.25-7.46(5H, m), 7.51(1H, brs), 7.67(1H, d, J = 8.0 Hz), 7.92(1H, s), 8.32(1H, s). |
| Example 19 | 3-119 | 3-(2-chloronicotinamido)benzoic acid | 2-iodo-4-(perfluoropropan-2-yl)-6-(trifluoromethyl)aniline | (CDCl$_3$, ppm)δ7.42-7.45(1H, m), 7.58(1H, t, J = 7.8 Hz), 7.76(1H, d, J = 7.8 Hz), 7.92-7.95(3H, m), 8.21-8.24(1H, m), 8.26(1H, s), 8.36(1H, s), 8.41(1H, s), 8.54-8.55(1H, m). |

Next, Formulation Examples, each of which includes a compound produced using the production method according to the invention as an active ingredient, are described below. However, the invention is not limited thereto. In the Formulation Examples, "part(s)" refers to part(s) by weight.

Formulation Example 1

20 parts of an amide derivative represented by Formula (3), 10 parts of polyoxyethylene styryl phenyl ether, and 70 parts of xylene were uniformly mixed, as a result of which an emulsion was obtained.

Formulation Example 2

10 parts of an amide derivative represented by Formula (3), 2 parts of sodium lauryl sulfate, 2 parts of dialkyl sulfosuccinate, 1 part of β-naphthalenesulfonic acid-formalin condensate sodium salt, and 85 parts of diatomaceous earth were uniformly mixed by agitation, as a result of which a wettable powder was obtained.

Formulation Example 3

0.3 parts of an amide derivative represented by Formula (3), and 0.3 parts of white carbon were uniformly mixed, and 99.2 parts of clay and 0.2 parts of DRILESS A (trade name, manufactured by Sankyo Agro Co., Ltd.) were added to the mixture. The reaction mixture was uniformly pulverized and mixed, as a result of which dustable powder was obtained.

Formulation Example 4

3 parts of an amide derivative represented by Formula (3), 1.5 parts of polyoxyethylene polyoxypropylene condensate, 3 parts of carboxymethyl cellulose, 64.8 parts of clay, and 27.7 parts of talc were uniformly pulverized and mixed. Then, water was added thereto, and the mixture was kneaded, granulated, and dried, as a result of which granules were obtained.

Formulation Example 5

10 parts of an amide derivative represented by Formula (3), 3 parts of β-naphthalenesulfonic acid-formalin condensate sodium salt, 1 part of tristyrylphenol, 5 parts of propylene glycol, 0.5 parts of a silicon-based defoamant, and 33.5 parts of water were sufficiently mixed by agitation. Then, the resultant was again mixed by agitation with a mixture of 0.3 parts of xanthan gum and 46.7 parts of water, as a result of which a flowable formulation was obtained.

Formulation Example 6

20 parts of an amide derivative represented by Formula (3), 6 parts of a naphthalenesulfonic acid-formaldehyde condensate metal salt, 1 part of a dialkylsulfosuccinic acid metal salt, and 73 parts of calcium carbonate were uniformly pulverized and mixed. Then, water was added thereto, and the mixture was kneaded, granulated, and dried, as a result of which a water dispersible granules were obtained.

When using the formulations thus obtained, the formulations are spread after diluted with water to 1 to 10000-fold, or are directly spread without diluting.

Next, the usefulness of the compound produced using the production method according to the invention as a pest control agent is specifically described with reference to the following Test Examples. However, the invention is not limited to these Examples.

Test Example 1

Insecticidal Test Against *Spodoptera litura*

A liquid formulation containing a test compound at a predetermined concentration was prepared, and cabbage leaves were immersed therein for 30 seconds and dried in air. Subsequently, the cabbage leaves were placed in a 7 cm polyethylene cup in which a filter paper was laid, and second-instar larvae of *Spodoptera litura* were released thereon. The cup was left to stand in a constant temperature chamber at 25° C., and the numbers of live and dead insects were examined after 6 days. The test was carried out in duplicate with 5 insects per group.

As a result of the test, the amide derivatives represented by Formula (3) and obtained in Example 9 and Examples 13 to 19, which were produced using the production method according to the invention, all exhibited a dead insect ratio of 70% or higher at a concentration of 1 ppm.

Test Example 2

Insecticidal Test Against *Plutella xylostella*

A liquid formulation containing a test compound at a predetermined concentration was prepared, and cabbage leaves were immersed therein for 30 seconds and dried in air. Subsequently, the cabbage leaves were placed in a 7 cm polyethylene cup in which a filter paper was laid, and third-instar larvae of *Plutella xylostella* were released thereon. The cup was left to stand in a constant temperature chamber at 25° C., the numbers of live and dead insects were examined after 6 days. The test was carried out in duplicate with 5 insects per group.

As a result of the test, the amide derivatives represented by Formula (3) and obtained in Example 9 and Examples 13 to 19, which were produced using the production method according to the invention, all exhibited a dead insect ratio of 70% or higher at a concentration of 1 ppm.

INDUSTRIAL APPLICABILITY

The amide derivative represented by Formula (3) which are obtained by the method of producing an amide derivative according to the invention exhibit excellent efficacy in pest control effect. That is, the method of producing an amide derivative according to the invention has high industrial utility.

The invention claimed is:

1. A compound having the following Formula (12):

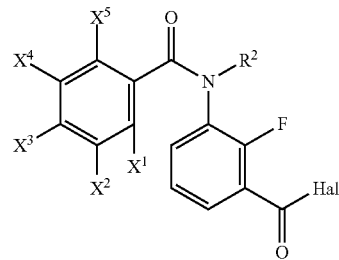

wherein, in Formula (12), $R^2$ represents a hydrogen atom or a methyl group; Hal represents a chlorine atom; $X^1$, $X^2$ and $X^5$ each represent a hydrogen atom; and $X^3$ and $X^4$ each independently represent a hydrogen atom or a fluorine atom.

* * * * *